US012616392B2

(12) United States Patent
Gjerde et al.

(10) Patent No.: US 12,616,392 B2
(45) Date of Patent: May 5, 2026

(54) DEVICES, METHODS AND KITS FOR BIOLOGICAL SAMPLE CAPTURE AND PROCESSING

(71) Applicant: VosBio, Inc., San Jose, CA (US)

(72) Inventors: Douglas T. Gjerde, Saratoga, CA (US); Daniel Robert Bollinger, San Jose, CA (US)

(73) Assignee: VosBio, Inc., San Jose, CA (US)

( * ) Notice: Subject to any disclaimer, the term of this patent is extended or adjusted under 35 U.S.C. 154(b) by 890 days.

(21) Appl. No.: 17/932,772

(22) Filed: Sep. 16, 2022

(65) Prior Publication Data

US 2023/0091650 A1 Mar. 23, 2023

Related U.S. Application Data

(60) Provisional application No. 63/340,926, filed on May 11, 2022, provisional application No. 63/312,162, (Continued)

(51) Int. Cl.
| | |
|---|---|
| *A61B 5/097* | (2006.01) |
| *C12Q 1/6844* | (2018.01) |
| *C12Q 1/70* | (2006.01) |

(52) U.S. Cl.
CPC .............. *A61B 5/097* (2013.01); *C12Q 1/701* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 7,118,537 | B2 | 10/2006 | Baddour |
| 7,779,840 | B2 | 8/2010 | Acker et al. |

(Continued)

FOREIGN PATENT DOCUMENTS

| | | |
|---|---|---|
| CA | 2566804 A1 | 1/2006 |
| CN | 105726069 B | 3/2018 |

(Continued)

OTHER PUBLICATIONS

Office Action in GB2213664.2, mailed Aug. 29, 2023, 3 pages.

(Continued)

*Primary Examiner* — Jay B Shah
(74) *Attorney, Agent, or Firm* — David A. Roise; VLP Law Group LLP

(57) ABSTRACT

Breath liquid particles and vapor are captured in a device presenting a surface and chamber space that condenses or freezes the vapor and aerosol particulates. One or more breaths are exhaled through the device. Capture can be performed on the freezing surface immobilizing water upon contact. The chamber space within the device may freeze liquid breath particles and vapor to collect them. After collection, the liquid is gathered and collected either by draining, pushing, or centrifugal force into a vial. The liquid may be collected and combined with a sample preparation reagent such as a virus lysing reagent, an internal standard, etc. After collection, the sample is analyzed. Analysis may be performed by PCR, qPCR RT-PCR, RT-qPCR, LAMP or any nucleic acid detection method, mass spectrometry, spectrophotometry or any analytical tool or method. Nucleic acid amplification reagents may contain a lysing reagent such as acetonitrile.

37 Claims, 7 Drawing Sheets

Related U.S. Application Data filed on Feb. 21, 2022, provisional application No. 63/285,480, filed on Dec. 2, 2021, provisional application No. 63/246,251, filed on Sep. 20, 2021.

(56) References Cited

U.S. PATENT DOCUMENTS

| | | |
|---|---|---|
| 2003/0208132 A1 | 11/2003 | Baddour |
| 2009/0263279 A1 | 10/2009 | Kline et al. |
| 2012/0277617 A1 | 11/2012 | Eichler |
| 2017/0119280 A1 | 5/2017 | Ahmad et al. |
| 2021/0059560 A1 | 3/2021 | Allegra et al. |
| 2023/0091650 A1 | 3/2023 | Gjerde et al. |

FOREIGN PATENT DOCUMENTS

| | | |
|---|---|---|
| CN | 112716532 A | 4/2021 |
| GB | 2451249 A | 1/2009 |
| GB | 2451249 A9 | 3/2009 |
| GB | 2612897 B | 5/2024 |
| GB | 2627587 B | 2/2025 |
| WO | WO 2004/058125 A2 | 7/2004 |
| WO | WO 2008/099003 A2 | 8/2008 |
| WO | WO 2019/178247 A1 | 9/2019 |
| WO | WO 2020/099874 A1 | 5/2020 |
| WO | 2021089992 A1 | 5/2021 |
| WO | WO 2021/209564 A2 | 10/2021 |
| WO | 2022060917 A1 | 3/2022 |

OTHER PUBLICATIONS

GB, Combined Search and Examination Report for Application No. GB2213664.2, 8 pages, Mar. 13, 2023.

WO, International Search Report and Written Opinion for Application No. PCT/EP2022/075868, 14 pages, Jan. 20, 2023.

International Search Report and Written Opinion in PCT/EP2024/065807, mailed Sep. 12, 2024, 21 pages.

Intention to Grant dated Feb. 22, 2024 in GB2213664.2.

Notification of Grant dated Apr. 30, 2024 in GB2213664.2.

Intention to Grant dated Nov. 18, 2024 in GB2405487.7.

Notification of Grant dated Jan. 14, 2025 in GB2405487.7.

Combined Search and Examination Report in GB2405487.6, mailed Jun. 21, 2024, 8 pages.

McDevitt, et al., "Development and Performance Evaluation of an Exhaled-Breath Bioaerosol Collector for Influenza Virus," Aerosol Science and Technology, 2013, vol. 47, pp. 444-451.

DEVICES, METHODS AND KITS FOR BIOLOGICAL SAMPLE CAPTURE AND PROCESSING

FIELD OF THE INVENTION

The present invention relates to devices, methods and kits for capturing and processing biological samples from breath, in particular for capturing biological samples that are liquid, particulate or vapor.

BACKGROUND OF THE INVENTION

Sample collection for the detection of virus and other markers is sometimes difficult, especially for children. A breath sample is less intrusive and a desirable way to sample for virus. In principle if someone is shedding and exhaling virus, the person is infectious and may spread the viral disease. However, liquid from breath is not easy to collect. Current breath liquid collection is an arduous process taking time and effort of an individual breathing into an apparatus. In addition, breath generally contains a lower viral load than a saliva or nostril swab sample.

In current technology, there are limitations in capturing exhaled breath quickly and efficiently. For purposes of widespread, rapid testing for infectiousness, breath needs to be collected rapidly from large numbers of people. Many conventional systems recommend 5-10 minutes of breath to be collected prior to analysis, typically yielding a sample of 1 mL of liquid. Conventional systems may also require a cooling sleeve to be cooled in a freezer several times to provide cooling, making those systems impractical for large-scale use. Other devices for breath collection utilize similar or longer timelines, requiring at least 10 minutes each. Many such devices can collect only 1-2.4 μL/s liquid from breath, which is too small a sample for many purposes, where larger liquid volumes, e.g., 1 mL or more, need to be collected in order to remove and recover usable liquid biological sample for processing.

U.S. Pat. No. 7,118,537 describes a device for condensing samples of fluid from breath in which a sleeve surrounding a collection tube may be chilled, e.g., in a home refrigerator, to improve efficiency of collection.

Accordingly, there exists a need to capture the liquid particles and vapor quickly as 1 min or less from a breath sample for viral, bacterial, biological and chemical analysis. There further exists a need to quickly capture a large part (or all) of the liquid that is present in the breath sample is captured and available to be processed for detection.

SUMMARY OF THE INVENTION

Broadly, the present invention provides methods, devices and kits for collecting a biological sample, e.g., in the form of liquid particles, aerosol particles and/or vapor by capturing them in a device comprising a surface and chamber space that condenses or freezes the biological sample when a user exhales one or more breaths through the device. Capture can be performed on the freezing surface immobilizing water upon contact. The chamber space within the device may freeze liquid breath particles and vapor to collect them. The collected sample may be a frozen sample, a combination of liquid and frozen sample or liquid sample, for example depending on the temperature of a capture surface and the time between collection and processing. After collection, the liquid biological sample is gathered and collected for example, by draining, pushing, scraping or centrifugal force into a vial. The liquid may be collected and combined with a sample preparation reagent such as a virus lysing reagent, an internal standard, etc. After collection, the sample is analyzed. Analysis may be performed by PCR, qPCR RT-PCR, RT-qPCR, digital PCR, LAMP or any nucleic acid detection method, mass spectrometry, spectrophotometry or any analytical tool or method. Nucleic acid amplification reagents or associated reagents may contain a lysing reagent such as acetonitrile.

In a first aspect, the present invention provides a method for detecting a target in a biological sample obtained from breath of a user, wherein the method uses a device for collecting a biological sample from breath which comprises a tube adapted to allow the user to breathe into the device, a collection chamber in fluid communication with the tube, the collection chamber having a capture surface, wherein collection chamber is a closed end tube or ends in a vial, a cooling element capable of cooling the capture surface to a temperature below the freezing point of water and a turbulence inducer disposed in or around the tube to cause the flow of breath to become turbulent to enhance contact between the capture surface and the exhaled breath of the user, wherein the method comprises breathing into the tube to provide a biological sample when the breath of the user condenses or freezes on the capture surface of the collection chamber;

optionally allowing a frozen biological sample to melt to form a liquid biological sample for analysis;

optionally processing the frozen or liquid biological sample; and analyzing a volume of the biological sample to detect the presence of the target.

In a further aspect, the present invention provides a method for detecting a target in a biological sample from breath from a user, wherein the method comprises:

(a) directing at least one breath of at least 10 seconds from a subject into a breath collection device, wherein the breath collection devices comprise a collection chamber capable of capturing at least a portion of the at least one breath as frost or ice to form a captured volume;

(b) processing the captured volume to recover one or more components of the biological sample;

(c) analyzing the one or more components to detect the presence of the target, thereby detecting a target in a biological sample from the breath from a subject.

In a further aspect, the present invention provides devices for collecting a biological sample from breath of a user, the device comprising:

a tube adapted to allow the user to exhale their breath into the device;

a collection chamber in fluid communication with the tube, the collection chamber having a capture surface, optionally wherein collection chamber is a closed end tube or ends in a vial;

a cooling element capable of cooling the capture surface to a temperature below the freezing point of water; and a turbulence inducer disposed in or around the tube to cause the flow of breath to become turbulent to enhance contact between the capture surface and the exhaled breath of the user;

wherein the biological sample from the breath of the user condenses or freezes on the capture surface of the collection chamber.

In some cases, the tube has a first end for the user to exhale into the device and the collection chamber is a vial having an interior capture surface, the vial being disposed over a second end of the tube, wherein the flow of breath reverses around interior walls of the vial so that the biological sample condenses or freezes on the capture surface. The collection chamber may be an end of the tube or the tube may incorporate a vial, e.g. a removable vial for facilitating processing of the collected sample.

Additionally, or alternatively, the device further comprises a turbulence inducer disposed in or around the tube to cause the flow of breath to become turbulent to enhance contact between the capture surface and the exhaled breath of the user. This may be achieved using a turbulence inducer. The turbulence inducer may be a separate component to the tube or collection chamber, for example an insert, or may be provided by the tube or collection chamber having structures, e.g. a rough surface or protrusions, that affect the flow of breath passing over them to induce turbulent flow.

As explained further herein, in some instances, the collection chamber is a syringe barrel, the tube fits into the barrel of the syringe and the turbulence inducer fits around an outer surface of the tube.

In some cases, the tube is open at a first end to allow the user to breathe into the device and comprises a wall towards a second end to deflect the breath of the user over the capture surface to enhance contact between the capture surface and the breath of the user.

Additionally, or alternatively the vial and/or the tube are removable to facilitate processing of the biological sample or to provide a multi-use device through replacement of the vial and/or tube.

In a further aspect, the present invention provides a device for collecting a biological sample from the breath of a user, the device comprising:

a tube adapted to allow a user to exhale their breath into the device;

a collection chamber in fluid communication with the tube, the collection chamber having a capture surface, optionally wherein collection chamber is a closed end tube or ends in a vial;

a turbulence inducing insert disposed in the tube to enhance contact between the capture surface and the exhaled breath of the user; and a cooling element capable of cooling the capture surface to a temperature below the freezing point of water;

wherein the biological sample from the breath of the user condenses or freezes on the capture surface of the collection chamber.

In a further aspect, the present invention provides a device for collecting a biological sample from breath of a user, the device comprising:

a tube adapted to allow a user to exhale their breath into the device;

a collection chamber in fluid communication with the tube, the collection chamber having a capture surface; and a cooling element capable of cooling the capture surface to a temperature below the freezing point of water;

wherein the biological sample from the breath of the user condenses or freezes on the capture surface of the collection chamber; and wherein the tube is open at a first end to allow the user to breathe into the device and wherein the tube comprises an end wall towards a second end to redirect the breath of the user over the capture surface to enhance contact between the capture surface and the exhaled breath of the user.

In a further aspect, the present invention provides a device for collecting a frozen biological sample from breath of a user, the device comprising:

a tube adapted to allow a user to exhale into the device;

a collection chamber in fluid communication with the tube, the collection chamber having a capture surface having a surface area of less than 50 cm$^2$; and a cooling element capable of cooling the capture surface to a temperature between about −10° C. (optionally about −20° C.) and about −40° C.;

wherein the biological sample from the breath of the user condenses or freezes on the capture surface of the collection chamber within about 10 to 120 seconds to provide a biological sample having a volume of between about 20 μL and 250 μL, optionally 180 μL.

In a further aspect, the present invention provides a device for collecting a frozen biological sample from breath of a user, the device comprising:

a tube adapted to allow a user to exhale into the device;

a collection chamber in fluid communication with the tube; and a cooling element capable of cooling the capture surface to a temperature below the freezing point of water wherein the capture surface is cooled to a temperature between about −10° C. (optionally about −20° C.) and about −40° C.; and/or the collection chamber has a capture surface having a surface area of less than 50 cm$^2$; and/or wherein the biological sample from the breath of the user condenses or freezes on the capture surface of the collection chamber within about 10 to 120 seconds to provide a biological sample having a volume of between about 20 μL and 180 μL In a further aspect, the present invention provides the use of a device according as defined herein for collecting a frozen or condensed biological sample from breath of a user to detect a target in a biological sample.

In a further aspect, the present invention provides a kit comprising a device as described herein, wherein the kits comprises a plurality of disposable elements of the device and/or reagents for processing the biological sample. The disposable elements may comprise the collection tube, the turbulence inducer, the collection chamber and optionally a plastic mouthpiece cover.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

All of the references mentioned herein are expressly incorporated by reference in their entirety.

The present invention will now be described by way of examples and not limitation with reference to the accompanying examples and figures.

DETAILED DESCRIPTION OF THE INVENTION

Figure 1:
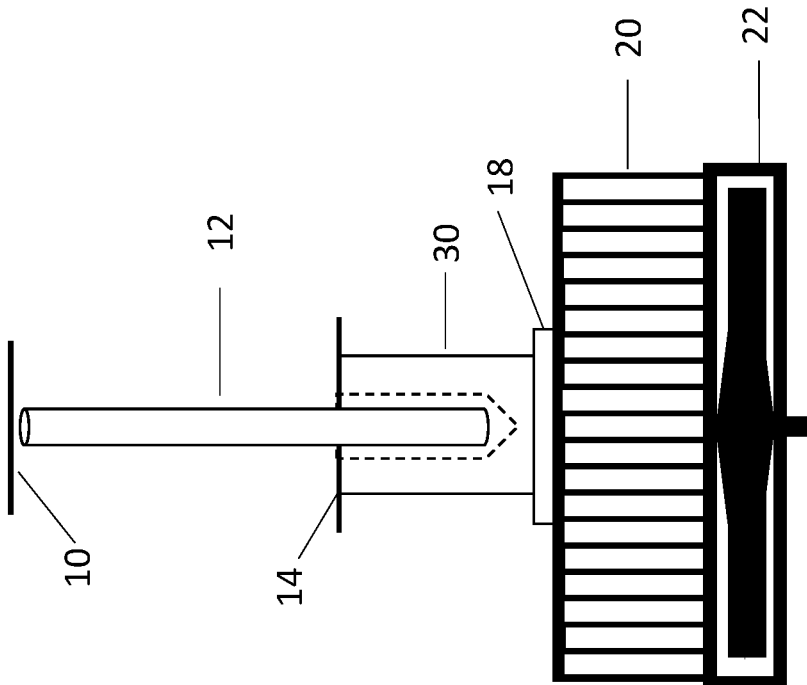
FIG. 1 shows a schematic of a device of the present invention in which a Peltier device is used to freeze a biological sample in a vial by introducing breath into the vial by a straw and water aerosol particles and vapor are captured.

Water vapor and water aerosol particulates are present in breath and can be deposited as liquid and/or ice/frost on a tube or vial wall when the temperature of the tube is significantly below the freezing point of water. In the devices of the present invention, tube or vial wall includes a collection surface capable of being kept at a temperature that is typically in the range of the $-10°$ C., $-15°$ C., $-20°$ C. to $-40°$ C. or colder. This means that water vapor, particulates and/or aerosol particles in the breath are deposited on a capture surface of a collection chamber where they can become solid and form ice crystals in the devices of the present invention or else condense on the cold capture surface, e.g. as droplets of liquid.

Advantageously, in order to collect breath condensate quickly and effectively, the freezing surface must be accessible to exhaled air, e.g., by arranging the collection chamber so that it is in fluid communication with a tube or straw through which the user of the device can exhale. Preferably, the device is adapted so that the capture surface can be maintained at the supercooled temperature to minimize the phenomenon that as frost is collected on the capture surface of the collection chamber, the temperature of the frost at the surface rises, potentially inhibiting the collection of further moisture and possible leading to inconsistent collection. It may also be advantageous to avoid the capture surface coming into contact with ambient air before collection takes places, to prevent a portion of the collected sample of frost to come from the ambient air, rather than from the breath of the user. To this end, in some cases, preferably the freezing capture surface is shielded from ambient air until the device sample is introduced to the collection surface so that the capture surface is protected from contact with air other than in the breath exhaled by the user. For example, in the devices of the present invention, a tube or straw is insertable into the device and into the collection vial past a barrier or shield to allow the delivery of the breath sample to the freezing capture surface. Prior to insertion of the tube or straw, the capture surface is effectively shielded from ambient air until the breath sample is introduced into the device. In one embodiment, the capture surface is a tubular vial with a means of collecting the liquid from the sample when removed from the freezing source, for example enabling the collection and processing of a sample having a volume of 200 μL or less, or having a volume of 250 μL or less.

In addition, in the prior art, it is very difficult to collect very small sample volumes with normal breathing apparatus sampling, with the result that large sample volumes must be collected over many minutes to enable downstream processing. The devices and methods of the present invention are capable of rates of sample collection of up to 2 μL/s, and more preferably up to 3-4 μL/s. After collection, the biological samples can be recovered as liquid and subjected to subsequent processing.

The collection structure of the devices of the present invention can take the form of a vial or a tube connected to a vial at the end of the tube. The terms "vial" and "tube vial" are used interchangeably in the present specification. In some embodiments of the invention the collection structure of the device is a tube. Alternatively, the collection structure of the device is a syringe barrel with the plunger barrel removed and the syringe bottom capped or sealed. The tube and/or vial of the apparatus is a supercooled surface that is a flat or curved, etc., smooth or rough surface and may contain grooves and depressions to facilitate collecting liquid. The outside of the tube and/or vial is cooled while breath is introduced inside with a breathing insert tube. In some embodiments of the invention the breathing insert is a (disposable) straw. Sample is directed into a tube and collected into the bottom of a vial. The freezing surface of the vial is protected from ambient air until breath is introduced. The shield is removed, and frozen breath condensate is collected. The breath enters the device in a laminar flow from the mouth. In some embodiments of the device the laminar flow is disrupted to produce turbulent flow as the breath flows across the cold surface. The introduction of turbulence may be performed as the breath reverses flow at the distal end of the collection tube vial. In some cases, the collection structure is a vial, e.g., a removable vial or the tube incorporates a collection vial.

The present invention described collects sufficient breath for analysis and virus detection with as little as 10 seconds up to 2 minutes of breath.

Materials collected in the liquid and frozen condensate could potentially include virus, bacteria, nucleic acids, organic compounds, volatile inorganic compounds, proteins, or biological materials, present in the breath. Those materials that are present in the breath will be collected by the device and method of the invention.

After collection, the sample is analyzed. Analysis may be performed on the collected materials to detect nucleic acids, utilizing devices that amplify and/or tag and then detect and optionally quantify. Other detection devices and methods include mass spectrometry, LC/MS, spectroscopy, UV and VIS spectroscopy, IR spectroscopy, gas chromatography, liquid chromatography, sequencing, next generation sequencing, culturing, colony counting, isothermal and thermocycling nucleic amplification, tagged and direct, hybridization, CRISPR, respiratory panel, etc. Applications of the technology include detection of viral and bacterial infections that spread by breath, as well as other disease states based on chemicals exhaled. Crucially, if infectious agents are being exhaled or coming out a person's mouth, by definition, the person is infectious. Virus or bacteria becomes airborne or spatters and can infect another person. The device may therefore be used as a tool for research and/or diagnostics.

The breath intake or sample inlet structure of the device of the invention may be vertical, horizontal or in between vertical and horizontal. A vertical breath intake may be positioned straight down into the device while horizontal is 90 degrees to the instrument. The collection tube to which the intake is connected may be positioned in any orientation. In some embodiments of the device, a horizontal or partly horizontal sample inlet may be employed. Partly horizontal shall mean the breath introduction is within 45 degrees of horizontal. In some embodiments of the device, a vertical sample inlet may be employed. This device will capture breath, gaseous water and liquid particulates. A horizontal mode allows the capture of breath without the capture of spit or dribble. In addition to being horizontal, the breath intake may include a depression or trap to capture spit or very large liquid particles.

In some embodiments of the device, a vertical sample inlet may be employed. Vertical intake means breath from the mouth is located directly above the apparatus and breath is directed down into the apparatus. Partly vertical shall mean the tube structure is within 45 degrees of vertical. A vertical or partly vertical breath entry orientation can be advantageous. In addition to capturing gaseous water and small airborne particulates, larger liquid particles, spit or droplets may also be captured. Some people spit or dribble as they breath, talk or sing. This can vary from person to person and with some people producing very large droplets while other people producing quite a lot of large droplets while breathing, talking or singing. In some embodiments of the device, the breath inlet mouthpiece may be constructed to capture breath exhaled and when speaking or singing. In some embodiments of the invention, the mouthpiece is constructed to cover a portion of the lips to facilitate sampling by a combination of breathing, talking and/or singing. A vertical or partly vertical capture breath inlet directs breath gas/liquid, small breath particulate and large breath particulate including airborne and spit particulate.

A vertical or near vertical breath intake capture device can capture breath gas/liquid, small breath particulates and large breath particulates, spit and dribble, thus measuring the potential infectiousness of different modes of disease expulsion from an individual while a horizontal or near horizontal breath intake capture device will limit capture to breath gases and liquid particles large enough to remain in the breath.

Regardless of how liquid particulates are introduced into the air or what type and how they are captured, the device of the invention may be used as a tool for research and/or diagnostics. For example, the viral infectiousness of a particular person depends not only on the ability of the virus to infect but is also a measure of the person to release and transport virus to another individual. Public health safety is affected more by the presence of infectious individuals in a crowd than by the presence of infected individuals in a crowd. The capture and collection of the water vapor and particles is efficient and effective. The collection is easy, meaning the procedure is quickly performed with minimal effort and no discomfort to persons providing breath samples.

In addition to liquid collection from breath, the sample liquid may be collected from ambient spaces. Air may be pumped through the device to collect and detect materials that may be present in the ambient air of a room or building or even outside a building.

Definitions

Efficient capture or collection means that a large part or all the water vapor and liquid present in the breath sample is captured.

Effective capture or collection means that the collection procedure can be done rapidly with collection and preparation of the sample for processing the sample in less than 10 minutes, less than 5 minutes, less than 2 minutes or less than 1 minute.

Ease of collection means that the procedure is quickly performed with minimal effort and no discomfort to persons providing breath samples.

The collection vial in the apparatus of the invention is any type of closed tube or structure where liquid can be collected directly from the collected sample. A tubular vial of the invention has a means to collect the liquid from the sample. Any method including gravity, scraping, momentum or centrifugal force may be used to coalesce and collect the liquid from the breath into the vial.

The collection tube of the apparatus/device of the present invention may be any type of tube or structure where liquid can be collected directly from the collected sample. In some cases, the collection tube may be a closed end tube or end in a vial.

Frost or frozen breath is defined as any water vapor or water aerosols that is collected from exhaled breath in the device and method of the invention. The water collected can be primarily or partially a solid, but also some portion may be in the form of liquid or may melt quickly when the device is removed from the cold source or as sample collection proceeds and the device warms.

Super cold temperature may be defined as being −10° C. or lower or being cold enough to capture at least some portion of the breath vapor or breath liquid particles as ice or frost, i.e., providing a frozen or partially frozen sample. Super cold temperatures can range from about −10° C. to −40° C.

The collection vial is defined as a chamber or vial where liquid from a breath sample can be directed for collection, additional processing or storage.

Although invisible to our eyes, water vapor and water particulates are always present in breath. The dew point is the temperature when liquid will form condensate from breath. Frost will be collected when the temperature is below the dew point and below the freezing point. Breath frost is water vapor and particulates that become solid and form ice crystals in the device of the invention or condenses on the cold capture surface. In the device and method of the invention frost is formed and collected from water and from air that is at ambient or body temperature when introduced into the device.

The device and method of the present invention capture water liquid from aerosol particles and vapor easily, efficiently and effectively from a breath sample for viral, bacterial, biological and chemical analysis. Efficient capture means that a large part (or all) of the water liquid present in the breath sample is captured and available to be processed for detection. It is important to collect all of the breath sample liquid in which virus, bacteria or chemicals may be present. If only the easiest collectible portion of the sample is collected, e.g., large liquid particles, then it is possible that a non-representative sample was collected.

As the present invention uses devices with super cold surface temperatures (e.g., in the sample capture surface or zone), collection is generally more efficient at the beginning of collection process and collection efficiency decreases as the volume of breath collected increases and sample is collected. The surface ice, frost or liquid formed will decrease the efficiency of collection because the temperature of the surface is warmed and can't be cooled as much or as quickly. In addition, as the devices of the present invention are generally small, this allows the water that is captured by the device to be more easily coalesced and collected for processing. This works against capturing liquid since the mass of the collection device is small because the device is small. As the device size decreases, the amount of liquid that can be collected also decreases. Capturing all or most of the water liquid in the breath may be efficient only for the first 10, 15, 20, 25 or 30 seconds or for the first 1, 2 or 3 minutes and then will decrease. However, by this time sufficient breath liquid and vapor is collected for detection of the desired material. All the captured liquid may be processed for detection. In some cases, the methods of the present invention comprise a further step of processing all or a portion of the captured liquid biological sample, for example to enable the detection of a target present in the sample. In some cases, at least 25% of the captured liquid sample is used for downstream processing. In some embodiments, at least 50%, 75%, 80%, 85%, 90%, 95% or an even greater percentage of the sample is processed, for example to improve the sensitivity of detection of the target present in the sample.

The capture or collection of the water vapor and particles is efficient in the device and method of the invention meaning that a large part or all the water vapor and liquid present in the breath sample is captured. The capture or collection of the water vapor and aerosol particles is effective meaning the collection procedure can be done rapidly. Collection of the sample may be performed in less than 5 minutes, less than 2 minutes, less than 1 minute, less than 45 seconds, less than 30 seconds, less than 20 seconds, less than 15 seconds or less than 10 seconds. Collection and preparation of the sample for processing can be performed in less than 10 minutes, less than 5 minutes or less than 2 minutes. Effective means that the collection and procedure can be done rapidly and the detection process may be initiated and started quickly after the start of sample collection, often in just a few minutes. The detection process may be initiated in less than 10 minutes or less than 5 minutes. This includes lysing of the sample with an organic solvent. PCR detection or LAMP detection which can be performed as quickly as 20 minutes; however, this technology is advancing rapidly, and detection times are likely to decrease further.

The cold surface area of the device of the invention is small because of the desire to capture and process small amounts of liquid. In some embodiments of the invention, the vial volume that liquid is collected into is 5 mL, 4 mL, 3 mL, 2 mL, 1 mL, 0.5 mL, 0.2 mL, 0.1 mL, 0.05 mL or less. In some embodiments of the invention, the cold surface area that ice forms on is 100 cm$^2$, 75 cm$^2$, 50 cm$^2$, 40 cm$^2$, 30 cm$^2$, 20 cm$^2$, 10 cm$^2$ or less. Although the temperature of the collection surface may increase as sample is collected, in some embodiments of the invention the initial temperature of the cold surface is below 0° C. In some embodiments, the initial temperature of the cold surface can be −10° C., −15° C., −20° C., −25° C., −30° C., −35° C., −40° C., −45° C., −50° C., −55° C., −60° C., −65° C., −70° C., −80° C. or colder. The capture surface of the collection chamber can be kept at a temperature between 0° C. and −80° C., between −15° C. and −70° C., or between −20° C. and −40° C.

To collect breath frost quickly and effectively, the freezing surface must be easily accessible. However, if a freezing surface is exposed, frost and liquid could inadvertently be collected from any ambient air. To prevent this, the surface may be shielded until the sample is introduced to the surface, for example with a barrier. However, once collection of ice starts, the collected ice on the surface raises the collection temperature, which lowers the efficiency of further collection. Further collection is possible, but collection may occur at a slower rate if the cold interior surface temperature cannot be maintained and is raised.

In addition, sampling very small volumes of liquid available from breath is difficult with normal breathing apparatus sampling. Frost formation on surfaces will prevent collection of further frost. In the device of the present invention, very small volumes of liquid are collected and manipulated. The volumes of liquid collected can be less than 200 µL, less than 100 µL, less than 50 µL, less than 25 µL, less than 20 µL, less than 15 µL, less than 10 µL or less than 5 µL. In the device and method of the invention, sufficient liquid can be collected from less than 10 exhaling breaths, less than 9, 8, 7, 6, 5, 4, 3, or less than 2 exhaling breaths. In the device and method of the invention, usable liquid can be collected from even 1 exhaled breath. Usable liquid from one adult's exhaled breath may be more than 100 µL and a significant portion, generally in the range of 20-80 µL, can be captured.

To achieve capture of these sample volume, the volume of the collection chambers of the devices of the present invention is generally smaller than those used in prior art devices that collect breath samples. In some cases, the volume of the collection chamber is between 0.5 mL and 50 mL, or a volume between 1 mL and 30 mL, and a volume between 5 mL and 20 mL, or a volume as set out in the table below.

| Name | Internal Diameter (cm) | Circumference (cm) | Cross-sectional Area (cm$^2$) | Length (cm) | Volume (mL) | Surface Area (cm$^2$) |
|---|---|---|---|---|---|---|
| 3 mL syringe | 0.83 | 2.61 | 0.54 | 7.50 | 4.06 | 19.56 |
| 3 mL inlet tube | 0.40 | 1.26 | 0.13 | 7.50 | 0.94 | 9.42 |
| 5 mL syringe | 1.18 | 3.71 | 1.09 | 6.00 | 6.56 | 22.24 |
| 5 mL inlet tube | 0.64 | 2.01 | 0.32 | 6.00 | 1.93 | 12.06 |
| 10 mL syringe | 1.45 | 4.56 | 1.65 | 6.70 | 11.06 | 30.52 |
| 10 mL inlet tube | 1.00 | 3.14 | 0.79 | 6.70 | 5.26 | 21.05 |
| 35 mL syringe | 2.29 | 7.19 | 4.12 | 10.47 | 43.12 | 75.32 |
| 35 mL inlet tube | 1.5 | 4.71 | 1.77 | 10.47 | 18.50 | 49.34 |

In one example, the collection chamber is devised from a 3 mL syringe barrel with an 8.3 mm internal diameter, cross sectional area of 0.54 cm$^2$, surface area of 19.56 cm$^2$ and volume of approximately 4.06 mL. The inlet tube has an internal diameter of 0.4 cm, external diameter of 0.54 cm. The turbulent inducers consist of flanges extending outside the inlet tube to a width of 0.72 cm.

In another example, the collection chamber is a 5 mL syringe barrel with an internal diameter of 1.18 cm and internal volume of 6.8 mL with a cross sectional area of 1.09 cm$^2$. The collection chamber's internal surface area is 22.24 cm$^2$. The inlet tube and turbulence inducer surrounding the inlet tube inserted within the collection chamber occupies approximately half of this volume. The internal volume of the central airway is 1.9 mL with a cross-sectional area of 0.32 cm$^2$. The inlet tube has an outer diameter of 7.9 mm and turbulence inducer flanges protrude to 10.75 mm. The cross-sectional area of the collection tube outside of the turbulence inducer is therefore slightly larger than the cross-sectional area inside the turbulence inducer's central air passage. This difference in cross-sectional area compensates for the increased turbulence in airflow once the breath leaves the central air passage and allows breath to flow easily and contact the cold surface without back pressure. Due to the ease of use and speed of capture, this is used in many of the examples of the invention.

In another example, a 10 mL syringe barrel serves as the collection chamber with an internal diameter of 1.45 cm, cross-sectional area of 1.65 cm$^2$, surface area of 30.52 cm$^2$ and 11.06 mL of actual volume. The inlet tube for this instance has an internal diameter of 1.0 cm and cross-sectional area of 0.79 cm$^2$. Flanges on the turbulence inducer extend to 1.4 cm to induce turbulent breath flow.

In another example, a 35 mL syringe barrel serves as a collection chamber. This syringe barrel has an internal diameter of 2.29 cm, cross-sectional area of 4.12 cm$^2$, volume of 43.12 mL, and surface area of 75.32 cm$^2$. In this example, the inlet tube has an internal diameter of 1.5 cm, cross sectional area of 1.77 cm$^2$, volume of 18.5 mL and surface area of 49.34 cm$^2$. This larger format option has lower initial efficiency than smaller versions, but experiences less decline in efficiency over multiple minutes of collecting breath.

In the device of the present invention, a freezing capture surface is presented to the breath by a vial or tube-like fixture or straw. The tube or straw inlet is effectively shielded from ambient air until breath can be introduced and presented into the device. This can be accomplished by having a barrier on the end of the straw or by simply having the straw long enough so that ambient air does not easily enter the device.

In one embodiment of the device, the capture surface is a tubular vial with a means of collecting the liquid from the sample when removed from the freezing source.

The freezing vial, tube or surface of the present invention apparatus is flat or curved, etc., smooth or rough and may contain grooves, baffles or depressions to facilitate collecting liquid. In some cases, the tube may be metal, glass or plastic and the wall thickness of the vial or tube may be 5, 3, 2, 1, 0.05 mm or less. The outside of the vial is cooled, and breath is introduced inside of the tube or vial. A disposable straw or tube inlet may be used to introduce the exhaled breath to the vial. Sample is collected into the vial. The freezing surface of the vial is protected from ambient air until breath is introduced. The shield is removed, and breath frozen and liquid condensate is collected.

Materials collected in the frozen and/or liquid condensate of breath may include virus, bacteria, spores, organic compounds, volatile inorganic compounds, proteins, and any other biological compound or material.

The collected breath liquid may be analyzed to detect nucleic acids. This may be performed by amplification or tagging. They may be quantified by various methods including LAMP, PCR, qPCR, RT-qPCR and any other detection device including next generation sequencing. Other detection devices and methods include mass spectrometry, LC/MS, UV, IR, etc. Applications of the technology include detection of viral or bacterial infections spread by exhaled pathogens, as by definition the subject would be infectious if these are present in the breath or the detection of organic molecules. The device may be used as a tool for diagnostics or research. The nucleic acid samples may be RNA or DNA. Preferably, the target nucleic acid is viral, for example where the virus is selected from the group consisting of COVID-19 (caused by Severe Acute Respiratory Syndrome Corona Virus-2, SARS-CoV-2), Acquired Immune Deficiency Syndrome (AIDS, caused by Human Immuno-deficiency Virus, HIV), cold sores, chickenpox, measles, flu, influenza, some types of cancer and others. Other examples include Herpes simplex, varicella-zoster virus (VZV), Respiratory syncytial virus (RSV), Epstein-Barr virus, Cytomegalovirus (CMV), Coronaviruses, Rotavirus, Hepatitis, Monkeypox, Marburg, Genital warts (human papillomavirus, or HPV), and BK virus. Examples of bacteria that may be detected using the present invention include tuberculosis (TB) or staphylococcus.

In addition to liquid collection from breath, liquid may be collected from ambient spaces. Air may be pumped through the device to collect and detect materials that may be present in the ambient air of a room or building or even outside a building.

Cooling of the tube or vial collecting frost may be accomplished using a number of different strategies. These include but are not limited to a cold surface that has been super cooled including using a Peltier cooler, a circulating cooler containing liquid below water freezing temperature, circulating evaporation cooler, a device cooling from a device releasing gas such as compressed carbon dioxide, a device that contains or has been treated with liquid nitrogen or dry ice and other methods.

The device of the invention may be a stand-alone surface where a person comes to the device to introduce the sample. The device may be mounted in front of a mouth or in a room. The device may have one sampling input or multiple sampling inputs operated in parallel.

The duration of collection may be minutes but is capable of being quite rapid. In some methods of the invention the collection time is 5 minutes or less, 3 minutes or less, 2 minutes or less, 60 seconds or less, 45 sec or less, 30 sec or less, 15 sec or less, 10 sec or less, or even 5 sec or less to collect usable ice and liquid.

The sample and detection process utilizes collection by freezing, scraping or dissolving the ice by solvent and, optionally adding a lysing reagent and then analysis. Sample collected in a vial or tube may be centrifuged to coalesce the liquid and may be taken up to transfer with a pipette. Sample may be collected remotely and mailed or may be collected at the point of care. One sample may be collected, or several samples may be collected in parallel and processed in 96 or 384 well sampling instruments.

It is possible to capture and detect a virus directly without lysing or sample preparation. The freezing breath collection may keep a virus stable, can capture all chemicals, and can be done rapidly. The capture and processing can be done reproducibly because greater than 70%, greater than 80% or greater than 90% of the virus, bacteria or chemical can be collected. All of the sample can be processed and detected. Some portion of the virus can release the nucleic acid which can be detected. However, adding an organic solvent, acetonitrile for example, will kill or inactivate the virus so that the collected liquid is safe to handle. Methods, devices and kits useful for the processing of nucleic acid samples for storage and analysis, especially by amplification techniques, are described in our co-pending publication WO 2021/ 209564 (PCT/EP2021/059815 filed on 15 Apr. 2021), the whole content of which is incorporated by reference in its entirety.

Column sample preparation for nucleic acid can be used. Enzyme degradation of the virus protein can be used to release the nucleic acid before detection. In other approaches, the detection methods can involve essentially no sample preparation and the nucleic acid may be detected directly from virus or other materials containing nucleic acid. Other organics can be detected directly using mass spectrometry and other methods.

Processing small liquid volumes from breath is difficult and novel. By efficient capture and manipulation, the detection is sensitive and rapid. There is little or no sample preparation for spectrometric and chromatographic analysis. The collection chamber or vial of the invention may be placed into a 96 well configuration or 384 well configuration after collection. Analysis of the samples may be automated. The sample may be introduced directly into mass spectrometer or LC-MS, micro volume UV spectrometer or other light absorbing spectrometer. Nucleic acid detection requires only lysing of the virus and bacterial detection with an organic liquid such as acetonitrile. Detection may be with LAMP, RT-PCR, LC, LC-MS, GC, GC-MS, MS, IR, UV, FTIR, NMR or any analytical technology. Detection may be performed with Loop-Mediated Isothermal Amplification, Whole Genome Amplification & Multiple Displacement Amplification, Strand Displacement Amplification & Nicking Enzyme Amplification Reaction, Helicase-dependent Amplification, Recombinase Polymerase Amplification and SI BA Nucleic Acid Sequenced Based Amplification and Transcription Mediated Amplification.

In order to be most useful and provide a safe margin of infectiousness, the methods and devices of the present invention may detect a ten-fold lower viral shed rate than would be likely to cause infection for a given situation. For example, a teacher or student in a school would be infectious if they are shedding about 600 viral particles per minute. The methods could be used to collect 30 seconds of breath from each student and assess viral load. If that viral load is more than 300, the subject is considered infectious, therefore the present invention would report anything above 30 viral particles from this sample. For the most sensitive situations, such as plane or train travel, the methods of the present invention could test a full minute of breath and detect as little as 5 viral particles.

While many LAMP studies have shown a Limit of Detection (LOD) in the range of 100 viral particles, various techniques are available to increase this sensitivity to the level of detecting 2-3 viral particles. The present invention can incorporate state of the art techniques including fluorescent detection to increase sensitivity and specificity. Novel viral lysing agents, such as acetonitrile, will improve recovery of viral nucleic acid and further increase sensitivity.

For very small volumes the entire sample may be collected and processed. Detection may be quantitative or may be a simple yes or no that a material is present above or below a defined detection limit. Sampling may be rapid, i.e., time of sampling may be 4 min, 3 min, 2 min, 1 min, 45 sec, 30, sec, 20 sec, or less.

In some instances, the number of exhaled breaths is limited to capturing 1 exhaled breath, capturing 2 exhaled breaths, capturing 3 exhaled breaths, or capturing 1-10 exhaled breaths.

In the present the invention, small liquid volumes may be captured and processed from breath i.e., less than 500 μL, 400 μL, 300 μl, 200 μL, 100 μL, 80 μL, 50 μL, 40 μL, 30 μL, 20 μL, or 10 μL or in the range of 5-100, 10-100, 15-300 or 20-100 μL.

Breath liquid particles and vapor are captured as frost or ice and liquid with a tube vial using surface temperatures of $-10°$ C., $-15°$ C., $-20°$ C., $-25°$ C., $-30°$ C., $-35°$ C., $-40°$ C., $-45°$ C., $-50°$ C., $-55°$ C., $-60°$ C., $-65°$ C., $-70°$ C., $-80°$ C. or colder. Capture may be performed with an active cooling device taking heat away from the cooling surface at the same time sample is collected.

The end of the capture device may be blocked, and air does not pass through the vial, tube or syringe. Because the end is blocked, the breath capture device reverses or changes flow through device. Reverse breath flow reduces the diffusion distance to the cold surface. The air flow may be laminar or turbulent. Breath liquid from particles and vapor are deposited or drained directly into a vial drain or directly into a vial. The vial containing captured liquid may be used directly for processing and detection including nucleic acid detection. The vial may contain lysing solvent. The vial may contain amplification reagents.

A Peltier device or super cooling and freezing a vial is shown in FIG. 1. Ambient air is shielded from the device by barrier 10 and freezer cover 14. Collection vial 30 is cooled directly by a Peltier device 18. Collection vial 30 can be metal or plastic or another material or combination of materials. Breath is exhaled and introduced into the device by straw 12 and liquid aerosol particles and vapor are captured in collection vial 30. The device super cools the walls of collection vial 30 so that the sample is collected quickly. However, the capacity of the device is limited. Heat sink 20 draws heat away from the hot side of the Peltier device, and fan 22 blows air to cool the heat sink to ambient temperature.

Figure 2:
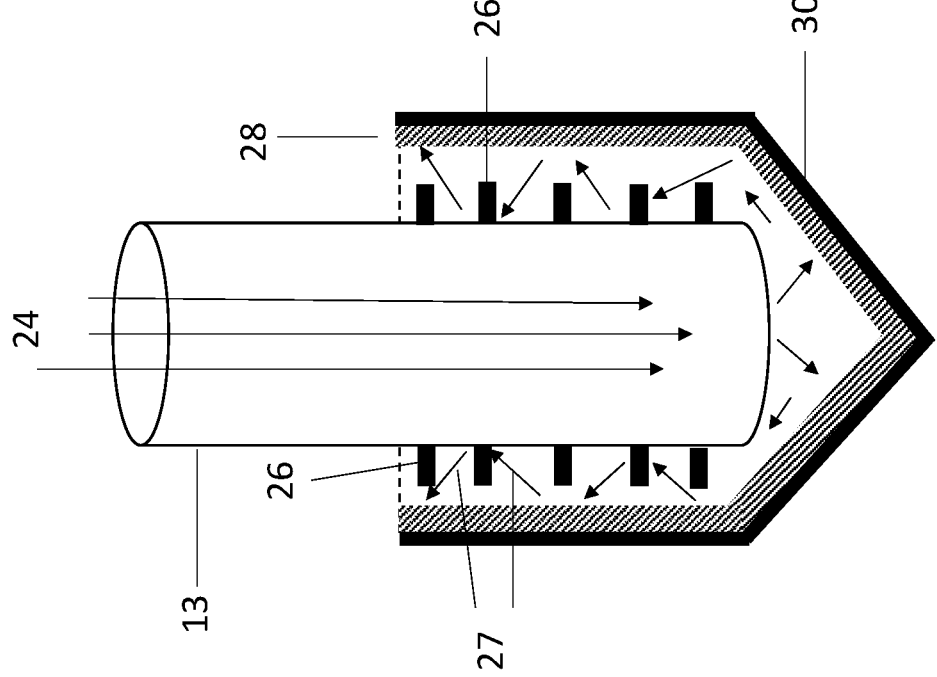
FIG. 2 depicts an enlarged portion of the device shown in FIG. 1 showing how the breath flows through the end of the straw and into the vial, with the biological sample captured as liquid and/or ice on the inside the vial.

FIG. 2 shows that breath flowing in direction 24 can be introduced into collection vial 30. The air flow reverses at the bottom of the vial and then moves along the wall of collection vial 30. The flow may be laminar. Turbulent air flow increases collection speed and amount. Turbulence inducers 26 may be positioned on the outside of inlet tube 13 as shown here or may be positioned on the inside surface of collection vial 30. The turbulent flow directions are indicated by arrows 27 and may be straight and/or random or may incorporate swirl motions in different directions. Ice and liquid 28 are collected on the inside of collection vial 30 at the wall.

Figure 3:
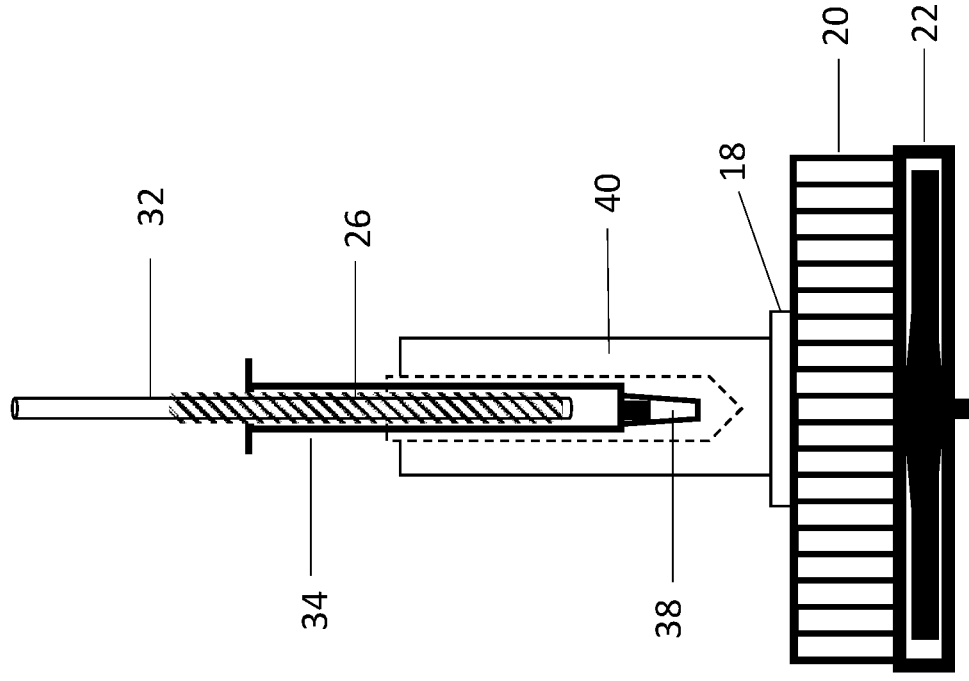
FIG. 3 shows an embodiment of a device of the present invention in which breath is introduced through a vertical straw into plastic, metal or glass tube vial refashioned from a modified syringe barrel. Air flow reverses near the end of the tube vial and passes through a turbulence inducer to increase contact with the wall surface.

FIG. 3 shows a device formed from syringe barrel 34 and vial with a closed end 38 essentially making the entire syringe barrel a vial with collection of liquid at the end. Copper or metal tube 40 is placed on top of Peltier device 18 to cool syringe barrel 34 and closed end vial 38. Breath is introduced with vertical tube 32. The inlet of vertical tube 32 may be round to place the lips around a tube or may be a mouth piece into or onto which the mouth may be placed. Air breath flow into tube 32 reverses near the end of closed end vial 38 and passes through turbulence inducers 26 to increase contact with the inside wall surface and space of syringe barrel 34 and closed end vial 38. The frost and liquid can be collected by gravity drainage, solvent washing, centrifugal force or a plunger may be inserted in syringe barrel 34. For example, a rapid plunger scraping motion may be used to force liquid into closed end vial 38. If a rapid plunger motion is used, closed end vial 38 may be loosened to allow air venting without allowing liquid to escape. Heat sink 20 and fan 22 are as shown in FIG. 1.

Figure 4:
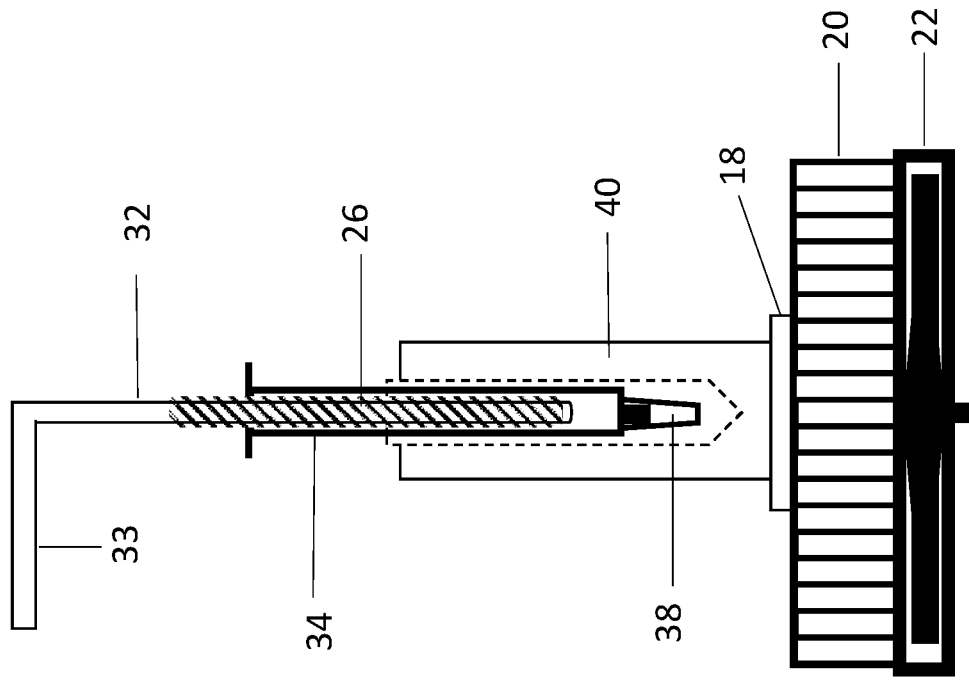
FIG. 4 is the device of FIG. 3 except the breath inlet is horizontal rather than vertical. The horizontal tube may include a liquid trap. The breath inlet of FIGS. 3 and 4 may contain a mouthpiece.
Figure 5A:
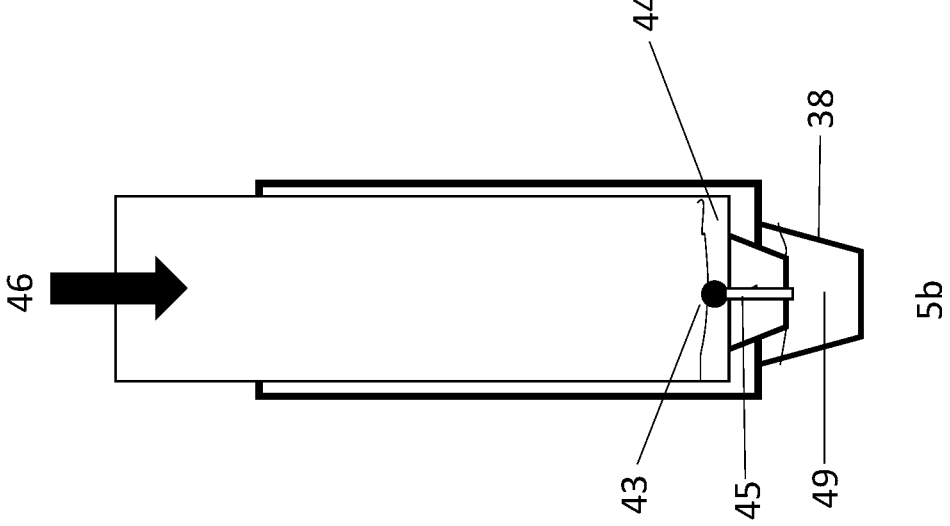
FIGS. 5a and 5b show a plunger that equalizes the total volume of collected liquid by redirecting any excess liquid.
Figure 5B:
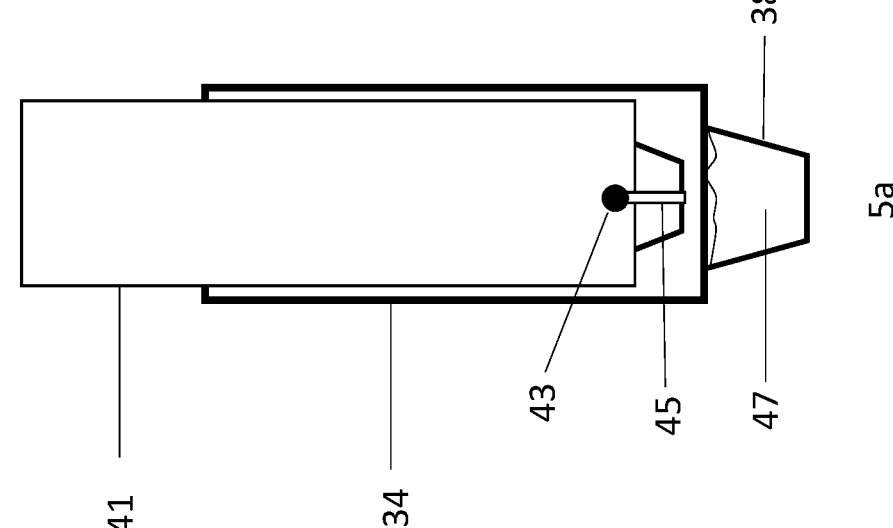

The device in FIG. 4 has all the same features as those shown in FIG. 3. Horizontal breath inlet 33 is used instead of a vertical breath inlet. The horizontal tube may include a liquid trap (not shown). The entrance of horizontal breath inlet 33 may be round to place the lips around a tube or may be a mouth piece into or onto which the mouth may be placed. FIGS. 5a and 5b show a device used to normalize the volume of liquid collected in a syringe barrel. FIG. 5a shows modified plunger 41 collecting liquid 47 from syringe barrel 34 into closed end vial 38. Relief tube 45 with top check valve 43 allows air to pass into modified plunger 41 as it is inserted. Collected liquid 47 may be scraped to drain into closed end vial 38. FIG. 5b shows further downward motion 46 of modified plunger 41 into syringe barrel 34 and closed end vial 38. The relief tube 45 with top check valve 43 now allows liquid to pass through the plunger 41 as it is inserted without permitting liquid to pass in the opposite direction. Excess liquid 44 passes through the plunger, leaving only pre-determined volume of collected liquid 49 in closed end vial 38. Closed end vial 38 may be removed to access liquid for further processing.

Figure 6:
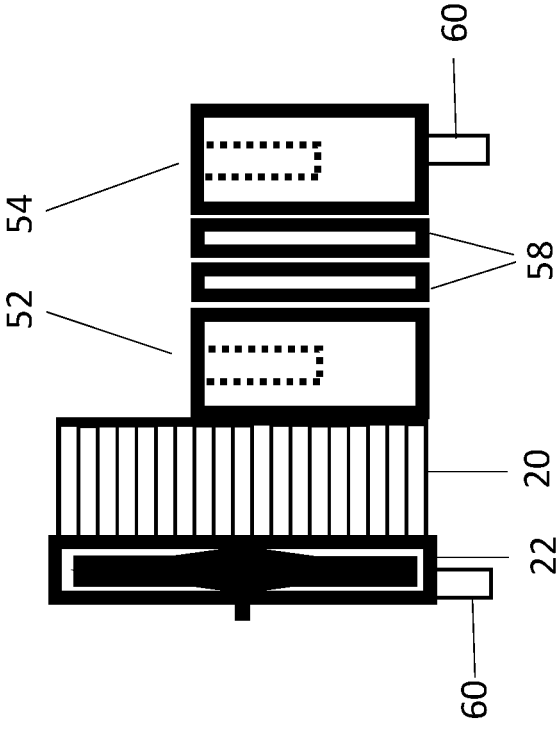
FIG. 6 shows a stacked Peltier collection cooler and reaction heater.

Stacked Peltier 58 with collection cooler 54 and reaction heater 52 supported by legs 60 is shown in FIG. 6. A single Peltier wafer will achieve the needed super freezing temperatures. However, stacking the thermoelectric module wafers can increase the cooling ability provided the heat is efficiently removed from the other side of the module. The hot side of reaction heater module 52 can be used to heat a reaction block. Heat is removed by heat sink 20 and fan 22. For example, the heated side of the device may be used to provide for LAMP detection by keeping the detection LAMP mixture at 65° C.

Figure 7:
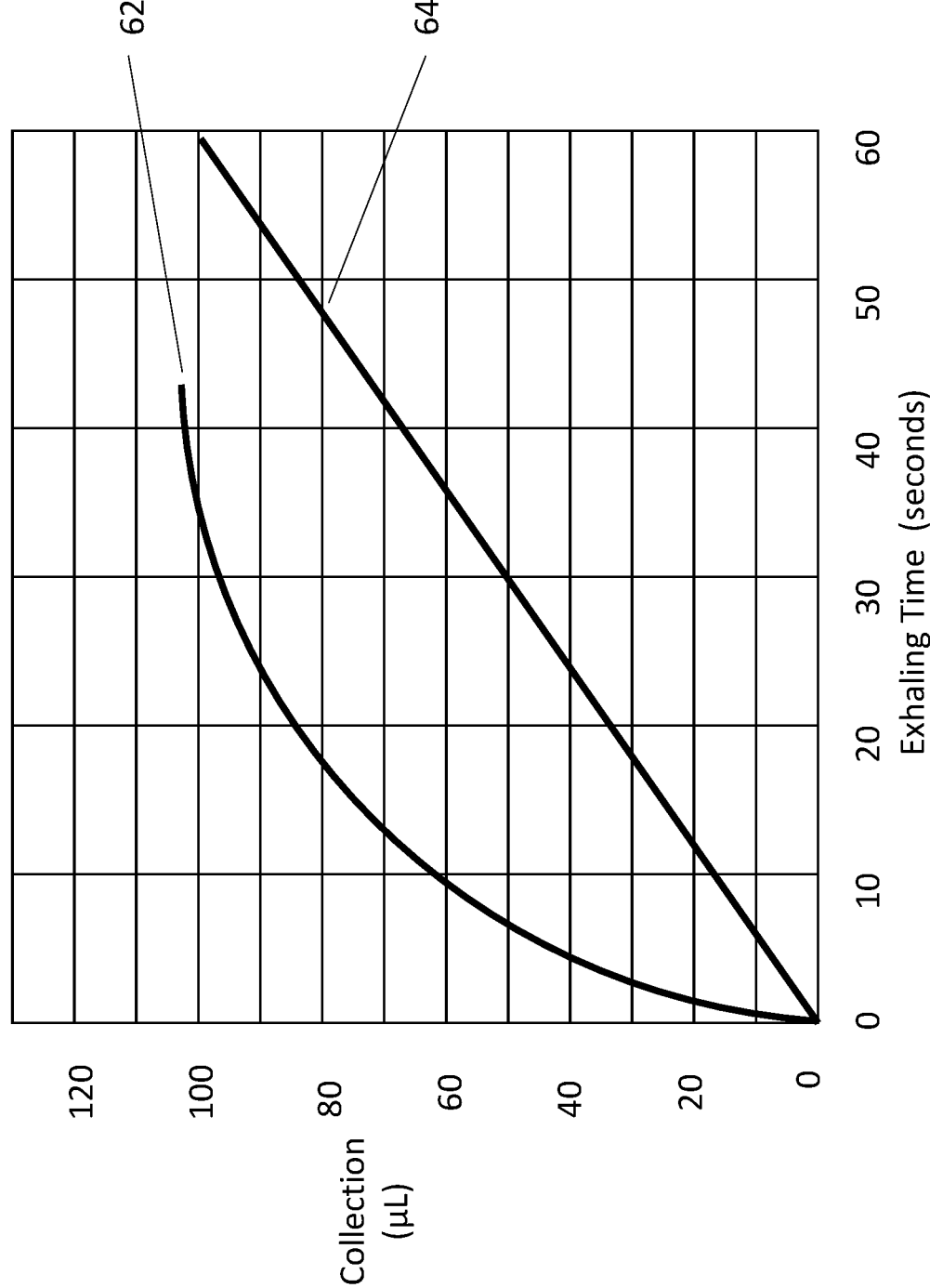
FIG. 7 shows the collection of liquid from the tube vial of the invention compared to a conventional tube.

FIG. 7 compares the collection of liquid from the syringe and vial of the invention in curve 62 compared to conventional EBC collection tube which is shown in line 64. The figure illustrates the difference of collection of liquid aerosol particulate and liquid vapor on the device of the invention vs. conventional device in the figure. Conventional devices have a large capacity to capture breath as liquid but also need this capacity to be able to collect and process the liquid. The device and method of the invention collects rapidly but because the device is small, it also quickly lowers the rate of collection. The figure shows the exponential collection of the present invention 62 vs. linear collection of conventional devices 64. The total amount of liquid that can be collected with the device of the invention is low, but sufficient liquid can be collected quickly. Exponential collection is rapid at first and then levels off. Rapid collection is possible, but collection quickly slows due to the insulating ice and liquid from the collected breath or low surface area. In addition, the surface needs to be shielded to prevent ambient liquid vapor from being collected as ice and preventing or slowing further capture of breath liquid and vapor. Because the capacity of the device of the invention is small relative to devices of the prior art, R-tube and other devices, capture of liquid from ambient air will lower the ability to capture additional breath liquid particles and vapor.

The workflow steps to the complete process to detect virus and bacteria include frost freezing and/or liquid capture, optionally lysing by organic solvent and direct detection without additional sample cleanup. The organic solvent will kill and deactivate the virus so that it is no longer capable of infecting. The workflow of the invention may detect RNA, DNA, chemicals, proteins, carbohydrates, virus, bacteria, spores, and all biomolecules.

Visible or fluorescent detection may be used. For high sensitivity, digital PCR may be used. Detection may be one sample at a time, or several samples in parallel. In some embodiments, groups are tested.

Sample processing and reporting may be done with an instrument or with a cell phone or smart device.

The detection and reporting may be done with a smart device tied to submitted samples and a subject's phone with identification. The subject's smart device may submit sample with a scan bar code, QR code to tie the sample to a person with reporting mechanism. A "yes" or "no" report can be given along with report giving guidance on distances to be safe. An initial report can be given with LAMP reporting if any highly infectious individuals are present, but LAMP analysis can continue to give yes and no answers at low infectiousness. The technology can quantify the amount of virus, DNA, RNA, bacteria or organic chemical in a room, aircraft or any interior space.

Active cooling is defined here as a process that adds cooling while the sample is being collected. Examples of active cooling include melting salt ice, dry ice, or Peltier coolers. A cold reservoir is a cold object that cools another while its own temperature increases. Examples include holding a cold (not frozen) beverage, or block of metal kept in a refrigerator or freezer. In some instances, the device may utilize a cold reservoir at −10° C., −20° C., −25° C., −30° C., −40° C., −50° C., −60° C., −70° C. or −80° C.

In some embodiments, ethanol or another liquid with a very low freezing temperature may facilitate heat conduction between the vial and cooling device. In other embodiments, the cooling surface may fit snugly against the vial.

Any smart phone or smart device equipped with a camera, internet connection, and able to run applications can be used for data analysis and reporting. The camera continuously monitors the reaction tubes for changes in color or fluorescence that would indicate a positive result. The application (app) processes the data from the camera, and reports to relevant parties.

The phone camera may continuously monitor 96 vial locations for example and identify them as either a fluorescent tube, a non-fluorescent tube, or an empty well. The app records the time that a new tube is added to the rack, and records the time when fluorescence becomes bright enough to detect. Depending on processing power, the app may quantify brightness over time from individual wells and calculate time of maximum increase in fluorescence. Either time point could estimate viral load in sample. By monitoring for both start and end-time, different samples may be run independently in parallel, with monitoring beginning as soon as each tube is added. At a predefined endpoint, such as one hour without fluorescence, a sample is considered negative. If a sample fluoresces, it is considered positive.

Once a positive or negative result is determined, various pre-defined groups may be automatically informed. The test subject typically receives a message, either through the app or via a text message generated by the app. In order to receive a message, the test subject must input their contact information and indicate informed consent for the test. Other people who were tested at the same site within a given period of time may also be alerted that they may have been exposed. If viral load has been quantified, level of exposure can be estimated. Depending on technical capabilities of location tracking, exposure may be estimated with more precision. For example, a person who has tested may receive a message stating "You appear to have spent 30 minutes within 1 meter of a person shedding 10,000 viral particles per minute. Your risk of infection is 50%". The test subject may be advised to wear a mask.

Data may also be sent to the organization conducting the test, as well as local health officials. If the test is conducted at a movie theater or airport, the movie theater or airport can be informed so they can take action to protect their patrons and follow sanitization procedures. Airports in particular may further contact airlines, including those operating specific flights to take action depending on whether the subject has already boarded a plane or not. The destination airport may also be contacted in advance, to prepare for potential exposure as the plane unloads. Companies may choose to make testing status of employees publicly accessible on the app. For example, "Steve the cashier tested negative at 10:30 am."

Data may also be reported to local health authorities or researchers as desired. If tests are widely used and recorded, they may add to the growing body of statistical samples for asymptomatic monitoring.

Test subjects may provide personal contact information as well as consent for reporting at the time of testing. In one instance, a phone number may be used, as it is a unique identifier as well as a convenient means of making contact. Test subjects may also download the app for more detailed information. If a user chooses not to use the app, he or she may receive text notifications regarding his or her test result, as well as notifications if there is a possibility of exposure. If a user chooses to use the app, he or she may access the current status of their test, as well as publicly available testing data. Tests in progress may be expressed in terms of decreasing possible viral load. For example, a high viral load of 40,000 virus may show a positive result after 10 minutes, so at 10 minutes with no positive result, the app can report that the viral load is less than 40,000. As time progresses, this maximum possible viral load will decrease. These numbers can also be expressed in terms of the time and distance that can be safely spent with other people, e.g.: "You are safe to spend 1 hour talking from 6 feet away from someone . . . You are safe to spend 1 hour standing 3 feet from someone . . . ".

Because time is both a function of probability of transmission and viral load, "safety distance" may be calculated. As time progresses from the beginning of the test, possible viral load decreases exponentially, if a positive result is not detected. The app may calculate in real time a maximum possible viral load and derive the minimum distance that the subject can safely maintain for that period of time. For example, the app may display in real time "You can safely stand 5 feet or 1.5 meters away from others!"

Experts believe that as few as 300 viral particles are sufficient to cause an infection of SARS-CoV-2. COVID patients have been recorded as exhaling between 60-25,000 viral particles each minute, leading to a wide range of probabilities for transmission. Probability of transmission from one person to another depends on rate of viral shed-ding, distance between the infectious person and the subject, time spent in contact, and volume of any room they may occupy together. These factors can be expressed in the following equation:

$$\bullet \ \text{Viral Exposure} = \text{shed rate} * \text{time}\left(\frac{1}{\text{distance}^3} + \frac{3 * \text{time}}{\text{volume}}\right)$$

(VE in viral particles, SR in Virus/minute, Time in minutes, distance in decimeters, volume in liters)

This equation can be used to determine what viral shed rate would be needed to infect another person under given conditions of time, distance, and room volume. For example, a person maintaining two meters distance in a large supermarket for one hour would not infect another person unless they were shedding at least 40,000 viral particles per minute, which would be considered a very high level. In contrast, a person sitting 50 cm from another in a moderately sized church for one hour may pass on their infection if they are shedding only 300 viral particles per minute. A passenger on a long train or airplane trip could spread their infection over the course of 12 hours with a shed rate of only 52 viral particles per minute.

Quantitative studies of viral load, whether sampling from breath, saliva, or nasopharyngeal swab have indicated that viral load tends to peak in the first few days of infection, then quickly falls to a lower level, before tapering off over several days. Presently, the general public has no means to estimate their level of infectiousness, and out of caution are encouraged to remain isolated for 10 to 14 days. A rapid, convenient, affordable, and quantitative test could permit recovering patients to estimate their own level of infectiousness, or screen for asymptomatic spread in large groups.

In some aspects, the present invention may be to detect diseases in which the infectious agent is exhaled, whether the agents are viral, bacterial, or fungal etc. Alternatively, in other aspects the present invention may be used as a research tool to develop diagnostics.

The sample may be collected in less than 5 minutes to capture breath liquid particles as frost or ice. Capture is in a vial or tube to collect breath and then coalesce liquid. Use of a vial is convenient to centrifuge, to coalesce liquid and then pipette to the detection device. This process may be automated. The use of a syringe tube to collect the frost is convenient to coalesce the liquid and deposit into a processing vial or detection device.

Breath may be directed into a device such as a disposable straw and collected in a disposable vial or tube. Several different turbulence inducers may be used to direct breath such that it may optimally contact the cold surface. In some instances, the cold surface is the internal surface of a 3 or 5 mL syringe barrel. In these instances, the syringe is sealed at the tip and the turbulence inducer can be inserted into the syringe. In one example, the internal barrel of the 3 mL syringe is 6.5 cm long, with an internal diameter of 0.9 cm. The turbulence inducer is 8 cm long and its tip is inserted completely into the bottom of the barrel of the syringe. The base protrudes 1.5 cm out of the syringe and widens to fit a paper straw in its opening. The interior of the breath direction device is a hollow tube with four vents at the tip. The exterior of the tube may have a variety of textures to optimize the breath's contact with the freezing external surface. Examples of similar devices are shown in FIGS. 1 through 4.

In one iteration, the external surface of the turbulence inducer is a screw-like helix, directing the breath along the longest possible route back out of the syringe barrel. The helix does not fit snugly against the inside of the syringe barrel, allowing some breath to leak past, which brings this air into direct contact with the freezing surface. This iteration may be twisted upon removal to minimize accidentally removing breath condensate. In another iteration, a series of baffles with small vents direct the breath toward the freezing surface, or to make sharp right angle turns, increasing turbulence. In another iteration, baffles are slanted at an angle resembling a herringbone pattern. This pattern again directs exhaled breath toward the freezing surface, while also generating pockets of high and low pressure, thus inducing turbulence. In this iteration, the turbulence inducer may remain in the syringe while it is centrifuged, and condensed liquid will be directed toward the tip.

The workflow steps required to complete the process to detect virus and bacterial samples, include the following: frost freezing capture of liquid from breath, collecting and coalescing the liquid, lysing in the coalesced liquid or detection vial then direct detection without additional sample cleanup. Because of efficient capture of liquid vapor and particles from breath it is possible to quantify the amount of virus, bacteria or organic chemical in a defined volume such as 1, 2, 3, 4 or 5 exhaled breaths.

It is possible to essentially capture all the liquid from the breath and process and quantify all liquid sample.

Some of the sample in the vial may be retained and stored or archived for possible future processing.

In another embodiment, a sample device may pump a defined amount of ambient air and freeze the liquid from the sample to collect sample to detect virus, bacteria, spore, nucleic acid, protein, biomolecule or organic chemical loading in a defined room.

The collection tube of the invention inlet diameter and tube length will have an effect on the collection capacity and resistance to breath inlet flow. In some embodiments, the tube size may be based on 1, 3, 5, 10 or 20 mL syringes or even larger syringe barrel volumes. As the syringe volume increases, commercial syringe barrel bodies have larger diameters. This can allow the breath inlet tube diameter to increase. This can be advantageous to lower the resistance of breathing into the tube. In some embodiments, the breath inlet tube diameter is increased to decrease the space between the inlet tube and collection tube so that breath can interact with the cool wall to collect the condensate.

Typical syringe sizes may be 3 mL or 5 mL. A 5 mL syringe collector has higher collection surface area and lower resistance to breath over 3 mL syringe. The time to collect 50 µL of breath condensate with a −15°, −20°, −30° C. or −40° C. cooling temperature may typically be approximately 15 seconds to collect 50 µL of breath condensate, 30 seconds to collect 100 µL of breath condensate and 60 seconds to collect 150 µL of breath condensate. While difficult to quantify, the resistance to breathing was slight for a collector based on a 3 mL syringe collector but was not noticeable for a collector based on a 5 mL closed end syringe collector. Larger tube collectors and diameters and lengths may collect larger volumes faster. A 10 mL syringe tube collector has higher surface area and lower backpressure, and higher breath liquid volumes may be collected.

Turbulence inducers placed inside the closed end collection tubes of the invention increase the contact of breath to the inside cool wall of the collection tube. In one set of experiments with a collector based on a closed end 5 mL syringe barrel cooled to −15° C., a helical turbulence inducer insert was tested compared to a straight straw insert. The turbulence inducer consists of a hollow tube with an internal diameter of 6 mm and external diameter of 8 mm, and a length of 65 mm. The mouth inlet was included in the design and produced by 3D printing. The external surface was a helical baffle extending 2 mm out, making 11 coils from the base of the tube to the tip. The base was attached directly to a mouthpiece, a tube with internal diameter of 12 mm and external diameter of 14 mm, and 40 mm long. The point of attachment between the mouthpiece and turbulence inducer includes wedge-shaped buttresses which allow the turbulence inducer to firmly press into place within the syringe. The tip includes four triangular vents to allow breath to freely disperse through the end of the syringe.

The helical design performance was compared to 6 mm inside diameter straight walled inlet straws. The 5 ml syringe collector was tested with 3 different turbulence conditions with 15 seconds of breath at approximately −15° C. Two trials with the helical turbulence inducer fully inserted yielded an average breath condensate of approximately 60 µL. Two trials of a straight wall straw fully inserted into the syringe barrel yielded on average 30 µL. Two trials of a straight wall straw inserted just past the opening of the syringe barrel yielded an average of 15 µL breath condensate. Thus, yields were increased with the introduction of turbulence of air passing by the cool surface of the collection barrel tube.

There are several different turbulence inducer designs, all of which were found to outperform a straight walled straw. These include helical with in channel disruptors, open chevon, staggered protrusions and random protrusions. In one design, the open chevron turbulence inducer had the same general dimensions as the helical design, but rather than a helix extending from the outer surface there were a series of broken chevron shapes. Each of these consists of a pair of wedges about 3 mm long. These wedges are arranged to direct breath in a turbulent path against the cold surface of the syringe, while permitting liquid to flow easily toward the tip of the syringe. There were 4 rows of these broken chevrons arranged from the base to the tip of the turbulence inducer, with 8 broken chevrons in each row.

Each version of the turbulence inducer was designed to achieve and balance two primary goals. First, the overall dimensions should minimize the back-pressure produced when blowing through the device. Second, the various baffles and flanges should disrupt the flow of air enough to create turbulence and maximize contact of the breath with the cold outer surface. In these embodiments, to minimize back-pressure, the cross-sectional area of the inner tube was approximately half of the entire cross-sectional area of the syringe. This allowed air to travel through a channel with consistent overall width.

The helical design directs the breath in the longest possible path along the surface of the syringe, thus maximizing opportunities for condensation. Because the turbulence inducer does not form an air-tight fit, a portion of the breath was able to pass over the helical baffles. This further encouraged the air to come into contact with the cooling surface, and for the breath to condense. In some versions of the helical design, wedge-shaped protrusions redirected a portion of the airflow from its smooth helical path. This caused the airstreams to interact with each other and form turbulence, again increasing contact between the air and cold surface.

In another design, vertical and horizontal baffles protrude from the exterior of the tube. In each case, there was an open channel for air to pass through, and this path was long and circuitous. The baffles were sloped in such a way as to encourage a significant portion of the air to pass around them, coming into direct contact with the cold wall.

After capture, the collection of liquid into the vial at the closed end can be performed with a scraping plunger or with a centrifuge. As described earlier, in a plunger collection where the vial at the end of the barrel is sealed, the plunger must allow air to escape as the plunger is depressed or inserted into the barrel. Using a centrifuge may cancel the need for a special plunger design. Insertion and processing the collected breath condensate with a centrifuge will move liquid to the collection vial and displace any air. No scraping with a plunger is necessary with application of centrifugal force. In some embodiments, the turbulence inducer does not need to be removed and the tube may be centrifuged directly to collect the liquid at the closed end vial.

The design of the turbulent inducer may enhance centrifugal force collection of liquid. The broken chevron design was one design suitable for coalescence and collection of captured breath liquid with a centrifuge, as it allows both turbulent airflow from the tip of the syringe to the opening and unimpeded waterflow from the opening to the tip.

Several custom centrifuge rotors were tested to collect exhaled breath condensate. Three different mounts were designed, and these were rotated on 3 different rotors. In the rotors tested in these experiments, the closed end capture tubes were on the same plane. In other embodiments, the capture tubes may be at an angle for easier insertion into the centrifuge. One battery powered rotor rotates at approximately 500 rpm, one hand cranked rotor can rotate at approximately 1000 rpm, and one AC powered rotor rotates at approximately 4,000 rpm. The mounts to hold syringes in place on the centrifuge rotor can have at least three basic arrangements. In one arrangement, the two syringes were each held in place 75 mm from the center of the mount, directly across from one another, and aligned with each other. In another arrangement, the syringes were mounted off-center, allowing them to be loaded more easily without interfering with each other. In this arrangement, the base of the syringe was 5 mm from the center of the rotor in the direction that the syringe was pointing and shifted 15 mm laterally. In the third arrangement, the syringes were mounted in a vertical stack facing opposite directions. The base of each syringe was mounted 5 mm from the axis of rotation.

Each mount design was tested on the battery powered, 500 rpm rotor. 100 μL of water were distributed along the length of the turbulence inducer before inserting it into syringe. Ten trials were then spun for 10 seconds with each style of mount; in-line, off-center, and vertically stacked. Then the water collected in the vial was measured. The vertical stack averaged 89.1 μL collected, off-center averaged 88.5 μL collected, and in-line averaged 94.7 μL collected. The difference between the in-line arrangement and the other two is statistically significant, although the difference between the vertical stack and off-center arrangement is not statistically significant.

Due to its geometry, the force at the base of the syringe is 15 times greater in the in-line arrangement than the other two, although there is only a twofold change at the tip. For bench-top convenience, a more compact, easy to load design such as the side-by-side arrangement may be desirable, although the in-line arrangement may be more effective.

In tests with exhaled breath condensate rather than manually adding droplets of water, the battery powered motor with the side-by-side mount performed less efficiently, capturing less than half of the exhaled breath. The rotor with a more powerful AC motor was substituted to be able to spin at 4000 rpm, an eightfold increase in speed. This allowed for 64 times the centrifugal force, which is sufficient to collect >99% of the exhaled breath condensate. The comparison is shown in Table 1.

TABLE 1

|  | Vertical Stack | Off-center | Straight-line |
| --- | --- | --- | --- |
|  | 89 | 77 | 95 |
|  | 80 | 82 | 92 |
|  | 91 | 92 | 97 |
|  | 88 | 91 | 98 |
|  | 90 | 93 | 90 |
|  | 81 | 90 | 96 |
|  | 87 | 91 | 94 |
|  | 99 | 90 | 95 |
|  | 94 | 85 | 98 |
|  | 92 | 94 | 92 |
| Mean | 89.1 | 88.5 | 94.7 |
| Std Dev | 5.66 | 5.44 | 2.71 |

Effect of Cooling Time for the Collection Syringe Barrel

In some instances, the syringe may be deposited into the cooling apparatus for a period of time prior to breathing through the mouthpiece. In testing with the broken chevron turbulence inducer in a 5 mL syringe, comparisons were made between blowing through the tube immediately after inserting it, waiting 20 seconds, or waiting one minute. In all cases, breath was collected for 20 seconds, and the apparatus was allowed to cool to −20° C. or lower between trials. On average, those trials wherein breath was collected immediately after inserting the syringe yielded 61.25 μL. In trials where the syringe was allowed to cool for 20 seconds, the average yield was 75.17 μL, which is a statistically significant increase over immediately sampling. Allowing the syringe to cool for a full minute did not increase yield over waiting 20 seconds.

Syringe Barrel Size Comparison

In one embodiment of the invention, a syringe barrel may be used for the closed end tube collection. The yield of exhaled breath collected from 3 mL syringes and 5 mL syringes was compared for various periods of collection time. In each case, a helical turbulence inducer was used, and liquid was collected using a plunger. When collecting for 10 seconds with the 3 mL syringe, the yield ranged from 32 μL to 46 μL, with an average of 40 μL. With a 15 second collection in the 3 mL syringe, the yield ranged from 30 μL to 65 μL, with an average of 49.5 μL. A 30 second collection with the 3 mL syringe yielded 60 μL to 84 μL, with an average of 67 μL. The 5 mL syringe had a range of 42 μL to 55 μL, with an average of 52.6 μL in 10 seconds. Collecting for 15 seconds from the 5 mL syringe, the yield ranged from 61 μL to 75 μL, with an average of 68 μL. When collecting for 30 seconds with the 5 mL syringe, the yield ranged from 60 μL to 83 μL with an average of 64.5 μL.

Syringe Dimensions

Two sizes of syringes were tested extensively: 3 mL and 5 mL. One 3 mL syringe has an internal diameter of 9 mm and a length of 70 mm. This gives it an internal surface area of approximately 19.8 cm$^2$. The 5 mL syringe has an internal diameter of 13 mm and length of 65 mm, with internal surface area of 26.5 cm$^2$. With larger syringe barrels the collection surface can be increased to 50, 100, 150 cm$^2$ or larger area.

23      24

Centrifuge Process and Mixing Reagents

The centrifuge process of coalescing liquids to the end of tube collection vial also provided a mixing capability. In one set of experiments a drop of food coloring gel dye was added to the top of the collected liquid and to the bottom of the collection vial. Centrifugal force was applied for 15 seconds. In both cases, the dye mixed thoroughly with the liquid giving a uniform color throughout. In addition, all air was removed. This method of mixing is useful to mix solvent, master mixes, or any preservative buffer or detection buffer.

Detection

Collected RNA and DNA may be detected by different methods including CRISPR-Cas-Based Nucleic Acid Detection, Rolling Circle Amplification, Helicase-dependent Amplification, Recombinase Polymerase Amplification. Loop-Mediation Isothermal Amplification, Real Time Quantitative Polymerase Chain Reaction, n-Counter (Nanostring), SMART-seq cDNA (Takara), Single molecule FISH (smFISH), single-molecule optofluidic chip, mass spectrometer with and without amplification, and any other suitable detection method. There are many detection methods under development and any of these would be suitable for detection and analysis of the nucleic acid. Liquid from the apparatus may be transferred to a vial or flow tube to facilitate detection and analysis. Proteins, carbohydrates, lipids and other bio substances may be detected from the collected liquid.

Sample Collection, Processing and Detection Process

The sample flow process using the device of the invention may proceed in different ways depending on the analyte and goals. Here are the steps of a full process:

1. Collect the breath sample
2. Optionally analyze directly
3. Optionally treat the sample
   a. Physical treatment such as heat
   b. Solvent treatment
   c. Enzyme treatment
   d. Chemical treatment such as tagging
4. Analyze the sample
   a. Analyze directly
   b. Optionally transcribe
   c. Optionally Amplify
      i. Analyze directly
      ii. Selective tag and analyze
5. Report the results
   a. Individual
   b. Venue Breath condensate is processed and collected by the device. The collected sample is analyzed directly or treated and then analyzed. The analyzed data is reported as yes/no and/or as a quantity.

Sample treatment before analysis is performed differently depending on the analyte and the detection process. Treatment with an organic solvent or other chemical agents or with heat may be used to release or lyse the sample and preserve the sample. In some embodiments samples may be treated or processed with nucleic acid sample preparation kits. The organic solvent is water miscible. The organic solvent may be acetonitrile. The organic solvent may be aprotic.

In some embodiments, nucleic acid reverse transcription may be performed directly or after sample treatment. In some embodiments, nucleic acid amplification, after the addition of amplification reagents, may performed directly, after sample treatment and/or after reverse transcription. Amplification may be performed by thermo cycling or isothermally. Detection may be a two-step detection e.g.

CRISPR or Illumina respiratory panel. In some embodiments, the analyte may be tagged and detected. Tagging may be done as part of the amplification process.

The sample matrix is water in most cases and the analytes are collected as part of the process of collecting water. The organic materials that are collected are soluble or at least compatible with the water sample matrix.

The analytes that may be detected include RNA, DNA, Proteins, carbohydrates, lipids, sugars, inorganic or organic molecules. The disease being tested may be associated with virus, bacteria, fungus, cancer and other biological diseases.

Testing can be done at many different types of venues to ensure safety. The venues where the invention may be used include, mass entertainment venues such as concerts, theme parks, cinema, transportation venues such as airports, ferries, trains and buses, high risk population venues such as hospitals, nursing homes, ICU and neonatal care facilities and other venues such as schools, community centers, churches, malls, public meetings, conventions and businesses.

In one embodiment of the invention, dry ice was added to the top of the Peltier cooler in the device shown in FIG. 3. In another embodiment of the invention, dry ice replaced the Peltier cooler in the device shown in FIG. 3. Peltier cooled devices may typically cool from ambient temperature to $-20°$ C. in approximately two-five minutes, whereas dry ice alone will cool the apparatus to $-60°$ C. or lower within a minute. In one experiment, a 20 second breath sample has increased the temperature of the Peltier cooled device by $4-12°$ C., whereas in the dry ice cooled device this sample increased temperature by $10-20°$ C., although in both cases the device returned to its baseline temperature within about 30 seconds. When both were tested with ethanol to facilitate thermal contact of the EBC collector and the device cooler, the device cooled with dry ice collected on average 95 μL in 20 seconds, whereas the Peltier cooled device collected 80 μL in 20 seconds. Some data of dry ice cooling with and without using ethanol for thermal contact is shown in Table 2 below.

TABLE 2

| | Time: 20 second<br>Breaths: 2 forceful breaths/test | | | | |
|---|---|---|---|---|---|
| Trial | Centrifuge slot # | Initial temp | Ending temp | EtOH | Volume recovered | Average collected (μL) |
| 1 | 1 | −47 | | No | 45 | |
| 2 | 2 | −44 | −37 | No | 75 | |
| 3 | 1 | −49 | −37 | No | 80 | |
| 4 | 2 | −39 | | No | 50 | |
| 5 | 1 | −42 | −30 | No | 55 | |
| 6 | 2 | −33 | −26 | No | 65 | |
| 7 | 1 | −25 | −25 | No | 55 | |
| 8 | 2 | −29 | −22 | No | 40 | |
| 9 | 1 | −34 | −27 | No | 60 | |
| 10 | 2 | −29 | −25 | No | 60 | 58.5 |
| 11 | 1 | −56 | −55 | Yes | 150 | |
| 12 | 2 | −57 | −56 | Yes | 60 | |
| 13 | 1 | −66 | −57 | Yes | 70 | |
| 14 | 2 | −60 | −58 | Yes | 90 | |
| 15 | 1 | −58 | −58 | Yes | 125 | |
| 16 | 2 | −60 | −58 | Yes | 105 | |
| 17 | 1 | −67 | −60 | Yes | 105 | |
| 18 | 2 | −63 | | Yes | 80 | |
| 19 | 1 | −66 | −60 | Yes | 85 | |
| 20 | 2 | −60 | −55 | Yes | 75 | 94.5 |

EXAMPLES

Example 1

A 40 mm square thermoelectric cooler, Peltier module TEC1-12706 was placed hot side down on a 70 mm square aluminum heat sink with cooling fan. A 20×20×15 mm freezing cube of aluminum with a 9.7 mm hole was placed on the cold side of the Peltier module. A round aluminum tube vial with dimensions 20 mm long and outside diameter 9.5 mm with a center hole with inside diameter 7.5 mm was placed into the freezing cube in an upright perpendicular position. A 7.75-inch-long Kraft paper straw with outside diameter of 6 mm was placed into the vial in an upright position. A 3D printed plastic fitting with vent holes kept the straw in the upright position. With this device, breath can be exhaled through the straw and into the internal wall of the cooled vial. Breath vapor and liquid particulates accumulated on the inside wall of the vial and the cleaned breath escaped to the top of the vial in the reverse direction. FIG. 1 shows the configuration of the collection device of the present invention used in the experiment.

In one set of experiments 12 V was applied to the Peltier cooler for 60 seconds. One breath was exhaled through the straw taking 8-12 seconds. The vial was removed and centrifuged for 10 seconds. 5 μL of liquid was coalesced and collected with a 20 μL pipette tip. Some liquid remained in the vial. The collected liquid was placed into a 0.2 mL PCR tube with 15 μL of master mix, solvent lysing solution and primers directed to detect the desired virus. RT-qPCR with a Chai Bio (Santa Clara, CA) 16 well instrument was performed in 40 minutes to detect the presence of virus.

In another experiment, the cooling was applied for 120 seconds, and 1.5 exhaled breaths collected. The experiment was performed 4 times. The vials were centrifuged each time the liquid was coalesced and collected. In two of the experiments 15 μL of breath liquid was collected. In another two experiments, sample sizes of 20 μL of breath were collected.

Example 2

Two stacked Peltier modules were attached to an aluminum heat sink with cooling fan on the bottom, with an 8 cm tall copper tube with internal diameter of 11 mm attached to a copper plate on the top. The tube was insulated with foam and 2 mL of ethanol were added to the tube. A 3 mL disposable Luer lock syringe, 7 cm long, 1 cm diameter was sealed with a cap and deposited into the tube, causing the ethanol to rise to the rim of the tube around it. The Peltier modules cooled the tube to approximately −40° C. A 3D printed plastic device for directing breath and inducing turbulence was inserted into the syringe, and breath was directed through for 15, 20, 25, and 30 seconds. After each trial, the syringe was removed from the tube and carefully dried. The plastic breath-directing tube was removed, and a plunger was partially inserted into the syringe. Next the cap was removed and replaced with a 200 μL PCR tube, which does not form an air-tight seal. The plunger was fully depressed, and the syringe was spun in a hand-powered centrifuge to elute all liquid. In these 5 experiments, a range of 40-90 μL of liquid were recovered, ranging from 2.5 μL/second to 3.6 μL/second.

Example 3

An aluminum tube 2.2 cm in diameter with an internal diameter of 1 cm, 8.8 cm long was cooled on dry ice to −40°

C. One end was plugged and 2 mL of ethanol were added to the tube to aid in thermal contact. A 3 mL disposable Luer lock syringe, 7 cm long, 1 cm diameter was sealed with a cap and deposited into the tube, causing the ethanol to rise to the rim of the tube around it. A 3D printed plastic device for directing breath and inducing turbulence was inserted into the syringe, and breath was directed through for 10 seconds. This experiment was repeated 6 times, and liquid yields ranged from 25-44 μL, or 2.5-4.4 μL/second.

Example 4

In another set of experiments, tubes made of two different metals were compared. A 3 mL disposable Luer lock syringe barrel, 7 cm long, 1 cm diameter was sealed with a cap and deposited into copper tube versus an aluminum tube, both cooled to −30 to −32° C. A 3D printed plastic device for directing breath and inducing turbulence was inserted into the syringe barrel, and breath was directed through for 15, 20, 25 and 30 seconds all using one exhaled breath. The collected volumes of liquid from the frost are shown in Table 3:

TABLE 3

| Copper | | Aluminum | |
|---|---|---|---|
| Time (s) | Volume collected (μL) | Time (s) | Volume collected (μL) |
| 15 | 41 | 15 | 31 |
| 20 | 51 | 20 | 64 |
| 25 | 89 | 25 | 59 |
| 30 | 85 | 30 | 77 |

The results also show that recovery of frost in the device of the invention is rapid at first and then tapers off as frost is collected. In this experiment, in both cases, sufficient liquid for analysis was recovered in 15 seconds.

Example 5

VosCryo Device and Process

The VosCryo is an example of an instrument of the invention for collection of exhaled breath liquid particles and vapor. Sampling often takes less than a minute or even less than 30 seconds to generate enough Exhaled Breath Condensate (EBC) for analysis. As the test subject blows through the mouthpiece, breath is directed against a cooled surface inside the syringe barrel and collection tube. Droplets and vapor from the breath condense on the cold surface. After collection, the condensate may be collected by scraping, draining or centrifuging, and the centrifuge allows rapid collection into a collection vial. This process consistently yields more than 50 μL of EBC sample that is ready for analysis using PCR, RT-PCR, RT-LAMP, RPA microbial culture, mass spectrometry, or other analytical tools. RPA (Recombinase polymerase amplification) is like LAMP and uses isothermal amplification but is performed at lower temperatures e.g., 30°–45° C.

For collection, a 3 mL syringe barrel with a cap or vial attached to the luer end fitting is placed closed end down into a vertical copper tube. The vertical copper tube was fixed perpendicular to copper plate cooled by a 24 V thermoelectric Peltier chip (40×40×4.7 mm, DigiKey 3.5 A 2223-CP354047-ND). The copper tube was ⅝" i.d., 9/16" o.d. and 3.5" length (height above copper base plate). The base plate on which the tube fits was ⅛" thick, 1.5" square. The Peltier chip is attached with an Artic Silver thermal paste to the underside of the copper base plate. The voltage was applied so that that cold is transmitted to the copper plate. Excess heat is removed from the hot side of the Peltier chip by an aluminum heat sink having radiator fins and a 90 CFM fan to blow air across the radiator fins. The Peltier used 3.8 A and the fan added 0.31 A for 4.1 A total. Thermal contact of the cold copper tube and the syringe inserted into the tube can be increased by adding an alcohol to the inside of the copper tube before inserting the closed end syringe barrel.

After collection, in some embodiments, a syringe plunger may be placed into the syringe to scrape the liquid and consolidate the liquid. In this case, the closed end of the tube is opened to let air escape, or the plunger is modified to allow air to escape along the plunger as it is being placed into the syringe. In some embodiments, a centrifuge is used to collect the liquid in a vial at the end of the tube.

In this example, apparatus and kit components to collect 50 breath samples were supplied as follows:

Packing List: Quantity

Apparatus: (1)

1. Cooling apparatus power supply and power cord

2. Low force two channel centrifuge side mounted on/off switch adapter for fit sample tube safety hinged cover direct power cord Operation was at 4000 rpm and 10 seconds Disposable Sampling Packet (50)

1. 3.5 mL syringe barrel

2. Turbulence Inducer with mouthpiece inserted into syringe barrel

3. Collection vial (attached to syringe barrel)

4. Plastic mouthpiece cover (to be removed before use)

Initial Apparatus Setup:

1. Plug in power cord to outlet and to power supply.

2. Plug in cooling apparatus to power supply, apparatus will begin cooling immediately.

3. Add 4 mL of alcohol (ethanol or isopropanol) into copper tube of apparatus. This assists in thermal transfer, as well as sterilization.

4. Allow about 6 minutes for apparatus to initially cool before collecting initial sample.

Sample Collection:

1. Tear open sealed sampling packet, hold syringe by plastic sleeve, and place in copper tube of apparatus.

2. Allow syringe barrel with mouth insert to cool for 10 or more seconds before taking breath sample.

3. Have test subject remove sleeve and blow firmly through mouthpiece for 20 seconds (about two deep breaths).

4. Typically, 20 seconds and two complete breaths is adequate to collect 50 μL of sample.

5. Children may need more breaths within the same time frame.

6. Multiple breaths or longer sample times will increase yield of sample.

7. Add 0.5 mL of alcohol to copper tube every 5 samples to compensate for evaporation.

Important guidelines for breathing samples:

1. When giving breath sample, blow firmly for as long as is comfortable.

2. Breathing into the apparatus should be comparable to inflating a balloon or spinning a pinwheel.

3. The goal is to fully empty the lungs with each breath.

4. Exhale through mouthpiece only. To inhale, either remove lips from mouthpiece or inhale through nose.

5. Gentle, tidal breathing results in lower yield of volume.

Factors influencing breath collection rate:

Temperature—Under normal ambient 20° C. conditions, the VosCryo collector cools to −20° C. within 6 minutes and continues to cool more slowly toward −40° C. The instrument collects a greater sample volume as the collection temperature decreases, ideally if the copper assembly temperature is below −20° C. It is recommended that the instrument be used between −20° C. and −40° C. Frost will form on the lip of the copper well within this temperature range. Under warmer ambient conditions, collection temperatures increase, and the collections times will need to increase. In another build of the VosCryo instrument cooling was below −20° C. within 2 minutes. Cooling continued to approximately −30° C. after 10 minutes, and eventually −40° C. after 15 minutes.

Time—Volume of EBC collected increases with sampling time. The following volumes were obtained at a starting temperature between −20° C. and −28° C., exhaling one complete breath within each 10 second period:

| Sampling time | Minimum expected volume |
| --- | --- |
| 10 seconds | 40 μL |
| 20 seconds | 70 μL |
| 30 seconds | 100 μL |
| 40 seconds | 120 μL |

Number of breaths—Collection rate is associated with the number of breaths sampled. One full breath every 10 seconds is recommended for sample collection. Note that collection volume generally increases with more breaths regardless of the breathing rate, although not in a linear fashion after approximately 50 μL is collected.

Lung capacity—Differences in physiology between test subjects may lead to variation in volume of breath, and therefore volume of EBC collected. If insufficient sample is collected from a given test subject, simply repeat sampling process to collect a larger sample. As warm breath is introduced into the apparatus, a small increase in the cooled copper temperature can be detected. The amount of energy can be quantified and correlated to the amount of breath introduced. In this manner a green light can indicate when the apparatus is cool enough to begin introduction of breath sample. Then, as the breath introduction proceeds, a yellow light can be shown to indicate by a slight increase in temperature of the apparatus. A red light can signify that sample introduction may stop and sufficient, specified sample volume has been collected. The appearance of the red light can be correlated to time, EBC volume, the amount of temperature increases and/or the amount of electrical energy needed to counter the warming of the apparatus by the volume of the warm breath introduced. In this way, sampling between individuals can be standardized. In any case, a minimum sample time with clear breathing instructions will produce sufficient volumes.

Sample liquid collection and processing:
1. Remove syringe from apparatus and place directly into centrifuge. Make note of sample number identification in centrifuge.
2. Ensure that centrifuge is balanced by either loading two samples or one sample and one unused syringe.
3. Close lid and ensure that green power switch is in ON position.
4. Hold black switch in front to activate centrifuge for 10 seconds.
5. Twist vial off the tip of the syringe. Collected liquid may be removed via pipette or stored with caps included.
6. Reagents including acetonitrile and reverse transcriptase, controls and amplification reagents may be added into the tube, pre or post centrifugation. Centrifugation will consolidate and mix all reagents.

COVID 2 standard with LAMP detection after acetonitrile treatment:
1. 10-20% acetonitrile lysing sample prep with 1-2% final acetonitrile detection concentration
Materials: NAT-rol COVID positive control (50 cp/µL), COVID LAMP primers (E and N), acetonitrile, 2× lamp mix, nuclease free water, 50× Fluorescent dye, 50× guanidine hydrochloride (New England Biolabs).
2. Prepare 50 µL of 10% acetonitrile in viral sample. Add 5 µL acetonitrile to 45 µL of sample, mix thoroughly by pipetting. Create 10% acetonitrile control by adding Add 5 µL acetonitrile to 45 µL water.
3. Add master mix, primers, incubate at 65° C. and detect. Positive is bright pink color.

Samples can be analyzed using LAMP, PCR, or other analytical tools. The EBC treated sample was analyzed by RT-PCR and RT-LAMP. Possible methods include PCR, RT-PCR, RT-LAMP, microbial culture, mass spectrometry, or other analytical tools including digitized nucleic acid amplification methods. Amplification methods may be performed with thermal cycling or isothermal. Some isothermal amplification methods include: NASBA, Nucleic acid sequence-based amplification is a method used to amplify RNA; LAMP, Loop-mediated isothermal amplification is a single tube technique for the amplification of DNA. It uses 4-6 primers, which form loop structures to facilitate subsequent rounds of amplification; HAD, Helicase-dependent amplification uses the double-stranded DNA unwinding activity of a helicase to separate strands for in vitro DNA amplification at constant temperature; RCA, Rolling circle amplification starts from a circular DNA template and a short DNA or RNA primer to form a long single stranded molecule; MDA, Multiple displacement amplification is a technique that initiates when multiple random primers anneal to the DNA template and the polymerase amplifies DNA at constant temperature; RPA, Recombinase polymerase amplification is a low temperature DNA and RNA amplification technique.

The invention claimed is:
1. A method for detecting a target in a biological sample obtained from an exhaled breath of a user, wherein the method uses a device for collecting the biological sample from the exhaled breath which comprises a tube adapted to allow the user to breathe into the device, a collection chamber in fluid communication with the tube, the collection chamber having a capture surface, a cooling element capable of cooling the capture surface to a temperature below the freezing point of water and a turbulence inducer comprising formations disposed within or around an outer surface of the tube to cause the flow of the exhaled breath to become turbulent to enhance contact between the capture surface and the exhaled breath, wherein the method comprises
breathing into the tube to provide the biological sample when the exhaled breath condenses or freezes on the capture surface of the collection chamber; and
analyzing a volume of the biological sample to detect the presence of the target.
2. The method of claim 1, wherein the tube has a first end for the user to exhale into the device and wherein the collection chamber is a vial having an interior capture surface, the vial being disposed over a second end of the tube, wherein the flow of the exhaled breath reverses around interior walls of the vial so that the biological sample condenses or freezes on the capture surface.
3. The method of claim 1, wherein the biological sample is a frozen sample, a combination of liquid and frozen sample, or liquid sample.
4. The method of claim 1, wherein the collection chamber has a volume between 0.5 and 50 µL.
5. The method of claim 1, wherein the tube is used in a vertical configuration.
6. The method of claim 1, wherein the tube is used in a horizontal configuration to enable capture of the exhaled breath without the capture of saliva or dribble.
7. The method of claim 1, wherein the tube is used in a configuration between horizontal and vertical.
8. The method of claim 1, wherein the turbulence inducer is an insert disposed around the tube.
9. The method of claim 8, wherein the collection chamber is a syringe barrel, the tube fits into the barrel of the syringe, and the turbulence inducer fits around the outer surface of the tube.
10. The method of claim 1, wherein the turbulence inducer comprises formations disposed within the outer surface of the tube sufficient to induce turbulent flow of the exhaled breath passing over them.
11. The method of claim 1, wherein the tube is open at a first end to allow the user to breathe into the device and comprises an end wall towards a second end to deflect the exhaled breath over the capture surface to enhance contact between the capture surface and the exhaled breath.
12. The method of claim 1, wherein the collection chamber, the tube, or both the collection chamber and the tube is removable.
13. The method of claim 1, wherein the method has a sampling time during which the user breathes into the device of 5 min, 4 min, 3 min, 2 min, 1 min, 45 seconds, 30 seconds, 25 seconds, 20 seconds, 15 seconds, 10 seconds, or less.
14. The method of claim 1, wherein the biological sample is captured in 6 exhaled breaths or fewer.
15. The method of claim 1, wherein the biological sample is a liquid sample, a particulate sample, or a vapor sample in the exhaled breath.
16. The method of claim 1, wherein the collection chamber is a removable vial.
17. The method of claim 1, wherein the cooling element uses thermoelectric cooling to cool the capture surface.
18. The method of claim 1, wherein the cooling element is a Peltier device.
19. The method of claim 1, wherein the capture surface is cooled to −10° C. or colder.
20. The method of claim 1, wherein the capture surface has a surface area of less than 50 cm².

21. The method of claim 1, wherein the device comprises a removable shield to protect the capture surface from ambient air until the biological sample is collected from the exhaled breath.

22. The method of claim 1, wherein the device is capable of collecting the biological sample at a rate of up to 2 μL/s.

23. The method of claim 1, wherein the cooling element is switchable to enable a frozen biological sample to be thawed for analysis.

24. The method of claim 1, wherein the biological sample comprises nucleic acids.

25. The method of claim 24, wherein the nucleic acids are RNA or the nucleic acids are DNA.

26. The method of claim 1, wherein the biological sample comprises virus, bacteria, yeast, tissue cells, or organic molecules.

27. The method of claim 26, wherein the bacteria is tuberculosis (TB) or staphylococcus.

28. The method of claim 1, wherein the biological sample comprises virus.

29. The method of claim 28, wherein the virus is selected from the group consisting of a Severe Acute Respiratory Syndrome Corona Virus-2, a Human Immuno-deficiency Virus, a measles virus, an influenza virus, a cancer virus, a Herpes simplex virus, a varicella-zoster virus (VZV), a Respiratory syncytial virus (RSV), an Epstein-Barr virus, Cytomegalovirus (CMV), a Coronavirus, a Rotavirus, a Hepatitis virus, a human papillomavirusvirus, and a BK virus.

30. The method of claim 1, wherein a final liquid volume of the biological sample collected from the exhaled breath is 250 μL, 125 μL, 100 μL, 80 μL, 60 μL, 40 μL, 20 μL or less.

31. The method of claim 1, further comprising analyzing the biological sample by loop-mediated isothermal amplification (LAMP), reverse transcription polymerase chain reaction (RT-PCR), liquid chromatography (LC), liquid chromatography-mass spectrometry (LC-MS), gas chromatography (GC), gas chromatography-mass spectrometry (GC-MS), mass spectrometry (MS), infrared (IR), ultraviolet (UV), Fourier-transform infrared (FTIR), or nuclear magnetic resonance (NMR).

32. The method of claim 1, wherein the biological sample is a frozen biological sample, further comprising:

allowing the frozen biological sample to melt to form a liquid biological sample for analysis.

33. The method of claim 32, further comprising:

processing the liquid biological sample.

34. The method of claim 1, wherein the collection chamber is a closed end tube or ends in a vial.

35. A device for collecting a biological sample from an exhaled breath of a user, the device comprising:

a tube adapted to allow the user to exhale their breath into the device;

a collection chamber in fluid communication with the tube, the collection chamber having a capture surface;

a cooling element capable of cooling the capture surface to a temperature below the freezing point of water; and a turbulence inducer comprising formations disposed within or around an outer surface of the tube to cause the flow of the exhaled breath to become turbulent to enhance contact between the capture surface and the exhaled breath;

wherein the biological sample from the exhaled breath condenses or freezes on the capture surface of the collection chamber.

36. The device of claim 2, wherein the collection chamber is a closed end tube or ends in a vial.

37. A kit for assembling a device for collecting a biological sample from an exhaled breath of a user, wherein the kit comprises a tube adapted to allow the user to exhale their breath into the device, a turbulence inducer comprising formations disposed within or around an outer surface of the tube, and a collection chamber, the collection chamber configured for insertion of the tube and having a capture surface configured for cooling to a temperature below the freezing point of water.

\* \* \* \* \*